(12) United States Patent
Teigen et al.

(10) Patent No.: US 11,337,712 B2
(45) Date of Patent: May 24, 2022

(54) ASPIRATION THROMBECTOMY SYSTEM AND METHODS FOR THROMBUS REMOVAL WITH ASPIRATION CATHETER

(71) Applicant: Penumbra, Inc., Alameda, CA (US)

(72) Inventors: Scott Teigen, West Fargo, ND (US); Steven Loisel, Castro Valley, CA (US); Stephen Pons, Alameda, CA (US); Ben Tompkins, Danville, CA (US)

(73) Assignee: Penumbra, Inc., Alameda, CA (US)

( * ) Notice: Subject to any disclaimer, the term of this patent is extended or adjusted under 35 U.S.C. 154(b) by 0 days.

(21) Appl. No.: 17/387,704

(22) Filed: Jul. 28, 2021

(65) Prior Publication Data

US 2021/0353323 A1 Nov. 18, 2021

Related U.S. Application Data

(63) Continuation of application No. 16/988,556, filed on Aug. 7, 2020, now Pat. No. 11,096,712, which is a (Continued)

(51) Int. Cl.
*A61B 17/22* (2006.01)
*A61M 1/00* (2006.01)
(Continued)

(52) U.S. Cl.
CPC ............... *A61B 17/22* (2013.01); *A61M 1/75* (2021.05); *A61M 1/76* (2021.05); *A61M 1/77* (2021.05);
(Continued)

(58) Field of Classification Search
CPC ......... A61B 17/00; A61B 17/22; A61B 17/32; A61B 17/32037; A61B 17/3498;
(Continued)

(56) References Cited

U.S. PATENT DOCUMENTS

| 3,042,042 A | 7/1962 | Blanck |
| 3,086,528 A | 4/1963 | Eichelman |

(Continued)

FOREIGN PATENT DOCUMENTS

| WO | WO 2014/151209 A1 | 9/2014 |
| WO | WO 2017/142874 A2 | 8/2017 |
| WO | WO 2018/019829 A1 | 2/2018 |

OTHER PUBLICATIONS

Thorpe, P.E. and Osse, F.J., 2007. Endovenous management of Iliocaval occlusion. In The Vein Book (pp. 559-574), Academic Press, 2006.

(Continued)

*Primary Examiner* — Sarah W Aleman
(74) *Attorney, Agent, or Firm* — Baker Botts L.L.P.

(57) ABSTRACT

An aspiration thrombectomy system, comprising an aspiration catheter having a proximal end and a distal end, wherein the proximal end of the aspiration catheter comprises a lumen configured to accommodate fluid, a vacuum source comprising a controllable vacuum valve, and a controller configured to detect a change in a connection between the aspiration catheter and the aspiration thrombectomy system, wherein the controller is further configured to change a pulsation protocol associated with the aspiration catheter responsive to the change in the connection between the aspiration catheter and the aspiration thrombectomy system, wherein the pulsation protocol specifies pressure variations and pressure patterns to modulate the vacuum valve to change a level of vacuum at the distal end of the aspiration catheter.

17 Claims, 19 Drawing Sheets

Related U.S. Application Data continuation of application No. PCT/US2019/043095, filed on Jul. 23, 2019.

(60) Provisional application No. 62/778,708, filed on Dec. 12, 2018, provisional application No. 62/702,804, filed on Jul. 24, 2018.

(51) Int. Cl.

| A61B 17/34 | (2006.01) |
|---|---|
| A61B 17/00 | (2006.01) |
| A61M 39/10 | (2006.01) |
| A61B 90/00 | (2016.01) |
| A61B 17/3203 | (2006.01) |

(52) U.S. Cl.
CPC ............ *A61M 1/774* (2021.05); *A61B 17/00* (2013.01); *A61B 17/32037* (2013.01); *A61B 17/3498* (2013.01); *A61B 90/06* (2016.02); *A61B 2017/00022* (2013.01); *A61B 2017/00561* (2013.01); *A61B 2090/064* (2016.02); *A61B 2217/005* (2013.01); *A61M 39/105* (2013.01); *A61M 2205/3334* (2013.01); *A61M 2205/3344* (2013.01)

(58) Field of Classification Search
CPC ...... A61B 2560/0462; A61B 2562/225; A61B 2017/00022; A61B 2017/22079; A61B 2017/0023; A61B 2017/00561; A61B 2017/32007; A61B 2090/0807; A61B 34/30; A61B 1/00097; A61B 1/00105; A61B 5/150267; A61B 2560/0266; A61M 1/00; A61M 1/0023; A61M 1/0031; A61M 1/0035; A61M 1/0037; A61M 1/0062; A61M 1/71; A61M 1/74; A61M 1/743; A61M 1/75; A61M 1/77; A61M 1/774; A61M 2205/3334; A61M 2205/3344; A61M 39/26; A61M 2039/261–266; A61M 2039/1005
See application file for complete search history.

(56) References Cited

U.S. PATENT DOCUMENTS

| 3,659,605 | A | 5/1972 | Sielaff |
|---|---|---|---|
| 3,955,574 | A | 5/1976 | Rubenstein |
| 4,315,506 | A | 2/1982 | Kayser et al. |
| 4,634,435 | A | 1/1987 | Ingraham |
| 4,935,005 | A | 6/1990 | Haines |
| 5,094,961 | A | 3/1992 | del Valle et al. |
| 5,536,242 | A | 7/1996 | Willard et al. |
| 6,206,014 | B1 | 3/2001 | Cameron, III et al. |
| 9,254,144 | B2 | 2/2016 | Nguyen et al. |
| 10,531,883 | B1 | 1/2020 | Deville et al. |
| 10,722,253 | B2 | 7/2020 | Deville et al. |
| 2001/0051811 | A1 | 12/2001 | Bonnette et al. |
| 2007/0129679 | A1 | 6/2007 | Bonnette et al. |
| 2008/0125695 | A1 | 5/2008 | Hopkins et al. |
| 2008/0243153 | A1 | 10/2008 | Nguyen et al. |
| 2010/0204672 | A1 | 8/2010 | Lockhart et al. |
| 2012/0041360 | A1 | 2/2012 | Gerg et al. |
| 2012/0138833 | A1 | 6/2012 | Matteo |
| 2015/0283309 | A1 | 10/2015 | Look et al. |
| 2015/0327875 | A1 | 11/2015 | Look et al. |
| 2016/0220741 | A1 | 8/2016 | Garrison et al. |
| 2016/0367272 | A1 | 12/2016 | Garrison et al. |
| 2017/0049470 | A1 | 2/2017 | Mallaby |
| 2017/0056032 | A1 | 3/2017 | Look et al. |
| 2017/0238953 | A1 | 8/2017 | Yang et al. |
| 2017/0354777 | A1 | 12/2017 | Ofek et al. |
| 2018/0015244 | A1* | 1/2018 | Isaza ................. A61M 16/0833 |
| 2018/0021098 | A1* | 1/2018 | Hemphill ............... A61B 34/35 606/41 |
| 2018/0024022 | A1* | 1/2018 | Beden ..................... G01M 3/02 73/40.5 R |
| 2019/0059703 | A1* | 2/2019 | Ting ................... A61B 1/00121 |
| 2019/0126006 | A1 | 5/2019 | Rehm et al. |
| 2019/0239910 | A1 | 8/2019 | Brady et al. |
| 2020/0009301 | A1 | 1/2020 | Yee |
| 2020/0093503 | A1 | 3/2020 | Deville et al. |
| 2020/0297362 | A1 | 9/2020 | Deville et al. |

OTHER PUBLICATIONS

Fornell, Dave, "Catheter-Based Clot Busting Therapies", Diagnostic and Interventional Cardiology, https://www.dicardiolosy.com/article/catheter-based-clot-busting-therapies, 2013.

Rioufol, Gilles, Bertrand Collin, Michel Vincent-Martin, Phillipe Buffet, Luc Lorgis, Isabelle L'Huillier, Marianne Zeller, Gérard Finet, Luc Rochette, and Yves Cottin. "Large tube section is the key to successful coronary thrombus aspiration: findings of a standardized bench test." Catheterization and cardiovascular interventions 67, No. 2: 254-257, 2006.

Haude, Michael. Mechanical Thrombectomy Catheter Systems, 2 Interventional Cardiology 58-60, 2007.

Simon, Scott, Casey Paul Grey, Trisha Massenzo, David G. Simpson, and P. Worth Longest. "Exploring the efficacy of cyclic vs static aspiration in a cerebral thrombectomy model: an initial proof of concept study." Journal of neurointerventional surgery 6, No. 9: 677-683, 2013.

Munich, Stephan A., Kunal Vakharia, and Elad I. Levy. "Overview of mechanical thrombectomy techniques." Neurosurgery 85, No. suppl_1: S60-S67, 2019.

* cited by examiner

ASPIRATION THROMBECTOMY SYSTEM AND METHODS FOR THROMBUS REMOVAL WITH ASPIRATION CATHETER

PRIORITY

This application is a continuation under 35 U.S.C. § 120 of U.S. patent application Ser. No. 16/988,556, filed 7 Aug. 2020, which claims the benefit under 35 U.S.C. § 365(c) of PCT International Application No. PCT/US2019/043095, filed 23 Jul. 2019, which claims the benefit under 35 U.S.C. § 119(e) of U.S. Provisional Patent Application No. 62/778,708, filed 12 Dec. 2018, and of U.S. Provisional Patent Application No. 62/702,804, filed 24 Jul. 2018, which are incorporated herein by reference.

TECHNICAL FIELD

The present invention relates generally to the field of medical devices and methods. More specifically, the invention described herein relates to devices and methods for controlling clot removal from a patient's vasculature by aspiration thrombectomy.

BACKGROUND

Stroke is a significant cause of disability and death, and a growing problem for global healthcare. More than 700,000 people in the United States alone suffer a stroke each year, and of these, more than 150,000 people die. Of those who survive a stroke, roughly 90% will suffer long term impairment of movement, sensation, memory, or reasoning, ranging from mild to severe. The total cost to the U.S. healthcare system is estimated to be over $50 billion per year.

Stroke may be caused by a blockage in a cerebral artery resulting from a thromboembolism (referred to as an "ischemic stroke"), or by a rupture of a cerebral artery (referred to as a "hemorrhagic stroke"). Hemorrhagic stroke results in bleeding within the skull, limiting blood supply to brain cells, and placing harmful pressure on delicate brain tissue. Blood loss, swelling, herniation of brain tissue, and pooling of blood that results in formation of clot mass inside the skull all rapidly destroy brain tissue. Hemorrhagic stroke is a life-threatening medical emergency with limited treatment options.

Aside from cerebral stroke, thromboembolism throughout the vasculature, in both arterial and venous circulation, is characteristic of numerous common, life-threatening conditions. Examples of potentially fatal diseases resulting from thrombotic occlusion include pulmonary embolism, deep vein thrombosis, and acute limb ischemia. Acute pulmonary embolism is a significant cause of death in the United States, with roughly 300,000 patients dying each year. Pulmonary embolism can be a complication from deep vein thrombosis, which has an annual incidence of 1% in patients 60 years and older. All of the aforementioned diseases are examples of conditions in which treatment may include aspiration or evacuation of clot and/or blood.

Of particular interest to the present invention, the Penumbra System® mechanical thrombectomy system is a fully-integrated system designed specifically for mechanical thrombectomy by aspiration. It is intended for revascularization of patients with acute ischemic stroke secondary to intracranial large vessel occlusion. A comparable system designed for the peripheral and coronary vasculature, the Indigo® System is also a mechanical thrombectomy aspiration system, designed for revascularization of patients with thrombotic occlusion of the peripheral vasculature. Both the Penumbra System and the Indigo System are commercially available at the time of filing the present provisional patent application and include aspiration or reperfusion catheters, aspiration tubing, other accessories, and an aspiration pump (sold under the tradename: Pump MAX™ aspiration pump or Penumbra Engine™ aspiration pump) for connection to the aspiration tubing and aspiration catheters. As illustrated in FIG. 1, the Pump MAX™ aspiration pump 10 includes a base unit 12 which encloses a vacuum pump (not shown) which operates offline voltage. The base unit has an on-off switch 14 and a separate knob 16 for adjusting the level of vacuum provided by the pump. The vacuum level can be read on a pressure gauge 18. Blood and clot are drawn into a collection canister 20 from an aspiration tube 22 (shown in broken line) which is connected to a reperfusion catheter (not illustrated) which has been introduced to the vasculature of a patient to aspirate clot. The blood and clot are drawn into the collection canister by a partial vacuum which is provided by a vacuum connector 28 on the base unit 12 which is connected to the vacuum pump, not shown. The vacuum from vacuum connector 28 is applied to a vacuum port 24 on a removable lid 26. The vacuum connector 28 is connected to the vacuum port 24 by an external vacuum tube 30.

Although very effective, clot aspiration using the Indigo System mechanical thrombectomy apparatus or other similar vacuum-assisted thrombectomy systems must sometimes be terminated due to the risk of excessive blood loss by the patient, especially when using large aspiration catheters. During aspiration thrombectomy, when the catheter tip falls out of contact with the thrombus or other occlusive material, the tip is exposed to healthy blood and full flow ensues. Under such conditions, the blood loss rate is excessive, and in some cases, may result in premature termination of the procedure. In one example, during a procedure when the catheter enters healthy blood and full flow ensues, the blood loss rate is in the range of 20-25 cc per second with an 8 French size catheter. With a maximum tolerable blood loss of 300-1000 mL, the catheter cannot run in unrestricted mode for more than approximately 20 to 50 seconds. When a physician operates the system manually, the aggregate blood loss may reach an unacceptable level before sufficient clot is removed. In addition, reliably identifying whether the tip of the catheter is in contact with clot or is undesirably aspirating healthy, clot-free blood is a significant problem, and such manual control is not optimum.

During other procedures using the Penumbra System, such as, for example, neurovascular procedures for treatment of ischemic stroke, excessive removal of blood is less of a risk, and the primary focus of the procedure is maximization of removal of occlusive material. Optimizing both technique and aspiration control are of upmost importance for successful removal of occlusive material.

Therefore, it would be desirable to provide improved methods and apparatus for controlling the aspiration of thrombus and clot using aspiration catheters in combination with pumping consoles. It would be particularly useful to provide systems and methods which limit blood loss during such aspiration procedures such as by automatically stopping aspiration while the aspiration catheter is not in contact with clot or thrombus. Additionally, it would be desirable to provide systems and methods which optimize system performance, and procedures for removal of occlusive material. At least some of these objectives will be met by the inventions described herein below.

The Penumbra System® as it is commercially available at the time of filing this provisional patent application is described in a brochure entitled "Science of Aspiration: The Penumbra System® Approach." Relevant patents and patent publications include: U.S. Pat. Nos. 4,574,812; 5,624,394; 6,019,728; 6,283,719; 6,358,225; 6,599,277; 6,689,089; 6,719,717; 6,830,577; 8,246,580; 8,398,582; 8,465,467; 8,668,665; 9,248,221; US2003/0050619; US2010/094201; US2014/323906; US2014/276920; US2016/0220741; US2017/0238950; US2017/049470; WO2014/151209; and WO2010/045178.

SUMMARY OF PARTICULAR EMBODIMENTS

The present invention provides systems and methods that improve catheter aspiration by enabling a longer procedure, by enhancing the ingestion of occlusive material, or both. In some examples, the amount of fluid flowing through an aspiration catheter under vacuum aspiration is monitored to determine whether the flow is unrestricted, restricted, or clogged. Depending on the determined flow state, the present invention may employ different techniques and methods to improve catheter aspiration. In one example, unrestricted flow is detected, and aspiration is automatically and temporarily restricted for blood saving purposes. This may beneficially prolong the time available to perform the procedure and thereby allow more complete removal of occlusive material. In another example, restricted flow is detected, and full vacuum aspiration is automatically applied. In yet another example, a clogged catheter is detected, and pulsed aspiration is automatically applied. This may beneficially enhance the ingestion of large, tough, or otherwise troublesome occlusions. Alternatively, pulsed aspiration, full aspiration, or restricted aspiration may be applied on demand by a user of the present invention.

In one example, the systems and methods of the present invention address the problem of excessive blood loss through dynamic aspiration cycling. The nature and flowability of the material being withdrawn by the aspiration catheter is monitored so that the system can either allow continuous aspiration when in clot, or sampling of extraction rate to determine whether the tip of the catheter is in contact with clot, in order to reduce the risk of excess blood loss. While determining and monitoring of blood flow rate is disclosed in the exemplary embodiments below, other measurements of the flowability and/or structural composition of the aspiration effluent, such as monitoring the collection chamber's volume, monitoring the collection chamber's fill rate, visually monitoring the aspiration tubing (clot is darker than fresh blood), or placing a strain gauge on aspiration tubing, could also be used.

The systems and methods of the present invention may respond to variations in flow rate, pressure, differential pressure, or other indicators of the composition of the material inside or adjacent to an aspiration catheter in a sub-second time frame to limit the unnecessary aspiration of blood during a thrombectomy procedure. The present invention may be useful with any thrombectomy, embolectomy, atherectomy, or other catheter or probe system where blood and clot are withdrawn wholly or partially by application of a vacuum to the proximal end of any reperfusion, aspiration catheter or probe for the purpose of clot extraction.

In a first aspect, the present invention provides a vacuum aspiration control system for use with a vacuum source and an aspiration catheter. The system comprises a flexible connecting tube, an on-off valve, a sensing unit, and a controller. The connecting tube is linear in an unconstrained configuration and is configured to connect the vacuum source to an aspiration lumen in the aspiration catheter. The on-off valve is configured to be operatively connected to the connecting tube, and the sensing unit is configured to determine flow rate within the connecting tube and to produce a signal representative of such flow, typically as either unrestricted flow, restricted flow, or clogged. The controller is connected to receive the signal representative of flow through the connecting tube and to open and close one or more on-off valve(s) in response to the signal. In one example, the controller is configured to automatically close the on-off valve to stop flow through the connecting tube when the signal indicates unrestricted flow, e.g. that primarily healthy blood or blood free of vessel-obstructing clot is flowing through the connecting tube and/or that the catheter is substantially free from contact with clot or other occlusive material. In another example, the controller is configured to initiate pulsed aspiration when the signal indicates a clog, which may be caused by some occlusive material in or adjacent to the catheter or connecting tubing.

The controller is typically further configured to automatically open the on-off valve at a predetermined interval to sample effluent material through the connecting tube and the valve will typically only remain open if the signal indicates a return to clot. The controller algorithm is capable of deciphering the difference between healthy blood and clot independent of aspiration source and the inner diameter of the attached catheter.

The sensing unit may comprise any one or more of a variety of sensors, including differential pressure sensors, acoustic (including ultrasonic) flow sensors, optical flow sensors, thermal flow sensors, magnetic flow sensors, sensors which detect circumferential expansion of the connecting tube, and the like. While differential pressures are described in more detail below, it will be appreciated that any sensing unit capable of detecting when flow or extraction rate through the connecting tube is excessive and/or clogged, would be suitable for use in the present invention.

In exemplary embodiments, the sensing unit comprises a pair of pressure sensors at spaced-apart locations along the connecting tube to measure differential pressure. The controller can calculate flow based on the differential pressure and, from this, determine whether the calculated flow rate indicates unrestricted flow, restricted flow, or a clog.

In another embodiment, the sensing unit uses optical sensors that measure transmission, absorption, or both of light to characterize the contents flowing through the connecting tube. In one such example, visible light is used determine whether flow contains clot or is primarily clot-free. Typically, flow with clot is darker, which is detectable by optical sensors. Alternatively, the optical sensors may infrared, ultraviolet, visible light, or some such combination to analyze contents within the connecting tubing.

In another embodiment, the sensing unit uses circumferential expansion sensors to determine the contents flowing through the connecting tube. The internal pressure of the connecting tubing and the contents flowing through it effect the circumference of the connecting tubing. Under strong vacuum, such as during a clog, the tubing may maximally contract. During high flow of primarily clot-free blood, the tubing may contract only slightly. During restricted flow, the clots and blood may cause a relative expansion of the connecting tubing.

The on-off valve may also take a variety of specific forms. Typically, regardless of form, the on-off valve will comprise an actuator, such as a solenoid actuator, that is powered to open the valve. The valve itself may take a variety of forms, including a pinch valve, an angle valve, or any one of a variety of other valves that provide actuation. Alternatively, the manual on-off valve may be provided that allows a user to initiate and/or terminate functions and features of the present invention.

In further exemplary embodiments, the controller may be configured to open the valve and hold the valve open until a flow pattern which indicates unrestricted flow is detected whereupon the controller closes the valve. The controller may be further configured to automatically re-open the on-off valve. For example, in what may be referred to as "sampling mode", the controller may be further configured to periodically sample, or test flow to re-characterize flow and determine if it is safe to recommence aspiration. For example, the controller may periodically test flow by opening the on-off valve for a fixed time interval, in one embodiment 150 milliseconds, to establish a "test" flow. The test flow is characterized and, if it so indicates, the on-off valve may be reopened into a "treatment" mode to allow continued aspiration treatment. If the system characterizes the flow as unrestricted, e.g. excessive, then the system will dwell in a closed configuration for a fixed time interval, in one embodiment between a quarter second and two seconds, before an additional pressure differential sample is taken.

In other instances, however, the controller may not be configured to automatically reestablish flow when safe conditions have been reached. For example, the controller may be configured to allow a user to reposition the aspiration catheter and, after repositioning, manually open the on-off valve (typically by actuating a switch which causes the controller to open the on-off valve) to resume aspiration treatment. In such instances, the controller may immediately return to the "sampling mode," however, and if the reestablished flow is characterized as unrestricted flow, the controller will again close the on-off valve, and the user can again reposition the aspiration catheter in order to engage clot and manually resume aspiration. Such systems will typically provide a manual switch which allows the user to manually open the on-off valve.

The controller may be configured to control two or more valves. In one example, the controller controls a first on-off valve between an aspiration catheter and a vacuum source and a second on-off valve between an aspiration catheter and a pressure source with a pressure at least above that of the vacuum source. The controller may alternate between opening the first on-off valve and the second on-off valve to generate pressure variations within an aspiration catheter or tubing adjacent to such a catheter. The controller may sample flow while the first on-off valve is opened to determine whether an attached catheter is still positioned in clot or otherwise occluded. The controller may hold the first on-off valve open and the second on-off valve closed if no occlusions or clogs are detected.

In specific embodiments, the vacuum aspiration systems of the present invention comprise a base unit which incorporates at least one on-off valve and the controller. The base unit will typically be configured to be mounted directly on or near a vacuum pump or console and will usually include a connecting cable in order to receive power from the vacuum console or line and optionally exchange information with the controller and the vacuum console. The connecting tube typically has a proximal end configured to connect the vacuum source and distal end configured to connect to the aspiration catheter. In such instances, the vacuum aspiration system will typically further comprise an external unit configured to be secured to the connecting tube at a location between the distal end and the proximal end thereof. Exemplary external units comprise at least a portion of the sensing unit. For example, the sensing unit may comprise a first pressure sensor in the base unit and a second pressure sensor in the external unit. In those instances, the controller will typically be configured to determine if a differential pressure exists based on the signals from the first and the second pressure sensor.

In a second aspect, the present invention provides a vacuum aspiration method. The vacuum aspiration method comprises engaging a distal end of an aspiration catheter against an occlusion in the blood vessel. A vacuum is applied through an aspiration lumen of the aspiration catheter using a vacuum source coupled to a proximal end of the aspiration lumen by a connecting tube. In this way, portions of clot and other occlusive material may be drawn into the aspiration lumen, through the connecting tube, and into a collection receptacle by the vacuum source. Flow through the connecting tube is sensed, and a valve is automatically closed to stop flow through the connecting tube when the sensed flow exceeds a determined value while the vacuum source remains on. Flow through the connecting tube will be later reestablished by opening the valve, and the steps are repeated until a desired amount of clot has been aspirated.

In a third aspect, the present invention provides an assembly for generating pressure differentials that may result in pressure pulses to execute an extraction cycle. The assembly may include a fluid injection apparatus, a mechanical displacement apparatus, gravity induced pressure head, or a combination thereof. A fluid injection apparatus may provide a source of relative positive pressure for a catheter currently or previously under vacuum aspiration. For instance, the fluid may be at a pressure above that of the vacuum aspiration system, between full vacuum pressure and ambient pressure, at ambient pressure, between ambient pressure and systolic pressure, at systolic pressure, or above systolic pressure. The fluid injection apparatus may utilize an aperture, a valve, a pump, a pressure chamber, or some such combination. A mechanical displacement apparatus may physically displace the volume of a catheter system to provide relative increases and decreases of pressure depending on the direction of displacement. In one example, a mechanical displacement assembly assists vacuum recovery after a catheter has had its pressure increased above the pressure of the vacuum source.

In some embodiments of the present invention, the controller includes an algorithm that is used to interpret pressure sensor signals to determine whether the contents flowing through a catheter should be characterized as unrestricted, restricted, or clogged. Generally, unrestricted flow is a high flow that may be characterized as excessive and may be primarily or completely comprised of healthy blood, clot-free blood, or blood free of vessel-obstructing clot that is not helpful to aspirate, restricted flow may be comprised of a mix of healthy blood and clot or other occlusive material, and a clog may be caused by a clot or other occlusive material within an aspiration catheter, partially within an aspiration catheter, adjacent to an aspiration catheter, or in other connecting tubing attached to the aspiration catheter. In some examples, healthy blood is blood with a low enough proportion of cross-linked fibrin such that it is not sufficiently integrated to cause ischemia or other similar vessel occlusions. When the algorithm detects unrestricted flow, it may cause the system to initiate a sampling mode. When the algorithm detects restricted flow, it may cause the system to enable full vacuum aspiration. When the algorithm detects a clog, it may cause the system to generate a variety of pressure pulses with an extraction cycle. The algorithm may be responsive and adaptable to changing circumstances, such as changing to a catheter of a different size mid-procedure. The algorithm may adjust sampling modes and pressure pulse magnitudes if the catheter state remains static, changes too quickly, changes to slowly, or improves as expected.

In specific aspects of the method, the present invention may remove clot and other occlusive material from a blood vessel that comprises a vein or an artery. Sensing of flow may comprise one or more of differential pressure measurement, acoustic flow measurement, optical flow measurement, thermal flow measurement, measurement of circumferential expansion of the connecting tube, and the like.

In preferred aspects of the method, sensing flow comprises measuring the differential pressure using a first sensor located proximate the vacuum source and a second sensor located on or adjacent the connecting tube between the vacuum source and the aspiration catheter.

In still further embodiments of the method, the resuming flow through the connecting tube comprises opening the valve for a sub-second interval, detecting when the sensed flow is characterized as acceptable, and automatically resuming flow. Automatically resuming flow typically comprises automatically detecting when the sensed flow can be characterized and the valve remains open as long as the flow is so characterized. Alternatively, resuming flow may comprise manually opening the on-off valve.

In further embodiments of the method, pressure differentials are generated by closing a valve to a vacuum pump, opening a valve to a source of pressure, wherein the pressure is at least above that of the vacuum, and then re-opening the valve to the vacuum pump. Alternatively, or in combination, pressure differentials are generated by mechanical displacement, wherein a volume of a chamber is reduced to increase pressure within a catheter and a volume of the chamber is increased to decreases pressure within a catheter, whereby the actuation of the mechanical displacement chamber results in pressure differentials. The pressure differentials may be tailored to have a specific or dynamic amplitude and frequency that facilitates the removal of clot or other occlusive materials.

DESCRIPTION OF EXAMPLE EMBODIMENTS

Some embodiments of the inventions of the present application are described below. For clarity, not all features of each actual implementation are described in this specification. In the development of an actual device, some modifications may be made that result in an embodiment that still falls within the scope of the invention.

Referring to FIGS. 2-6, a vacuum system 40 of the type useful with the apparatus and methods for controlled clot aspiration of the present invention will be described. The vacuum system 40 includes a vacuum console 42 and a blood/clot collection canister 44. The vacuum console 42 comprises an enclosure having a recess 48 which is shaped to removably receive the collection canister 44 as will be described in more detail below.

Figure 1:
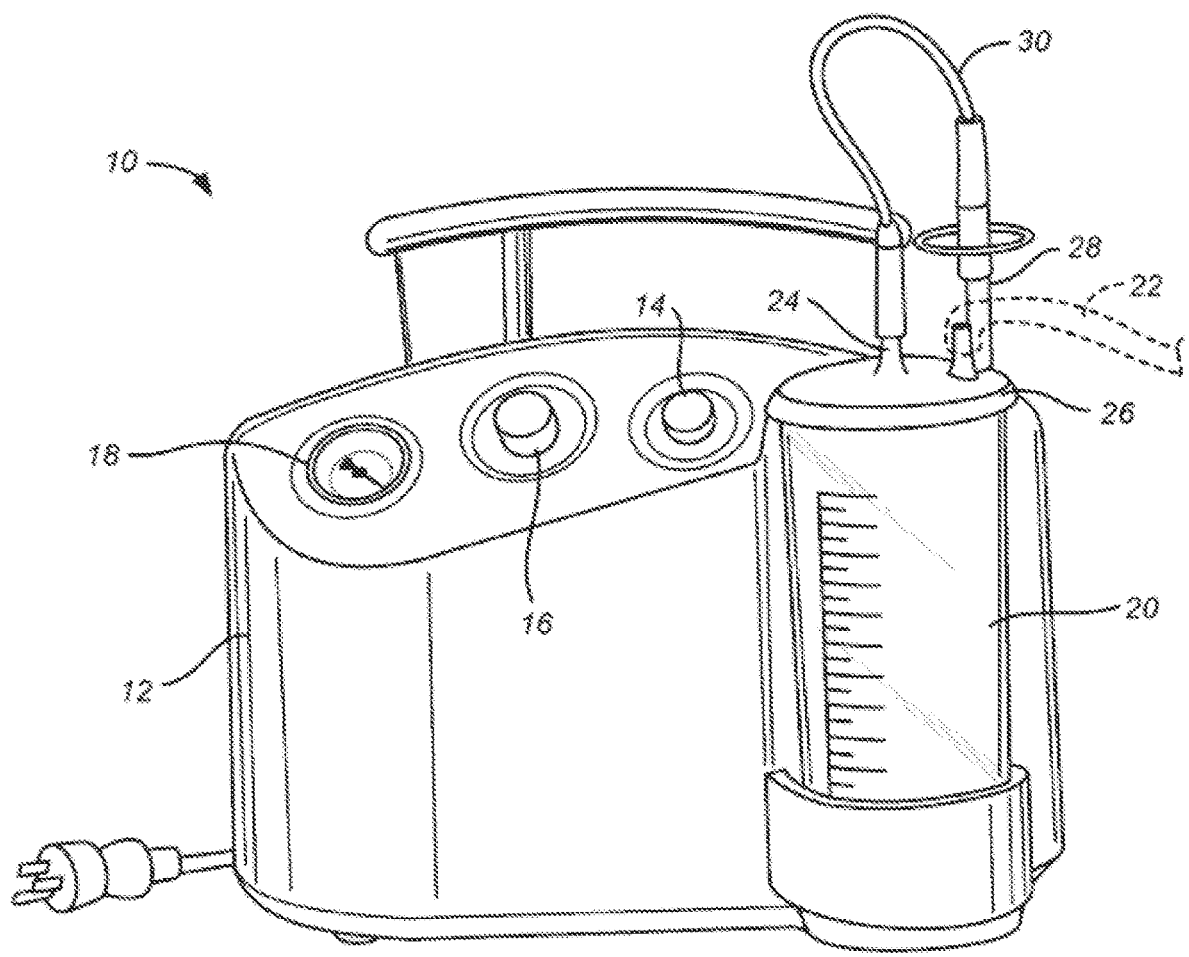
FIG. 1 illustrates the vacuum console and collection canister of the Penumbra System® mechanical thrombectomy system as described in detail in the Background of the Invention above.
Figure 2:
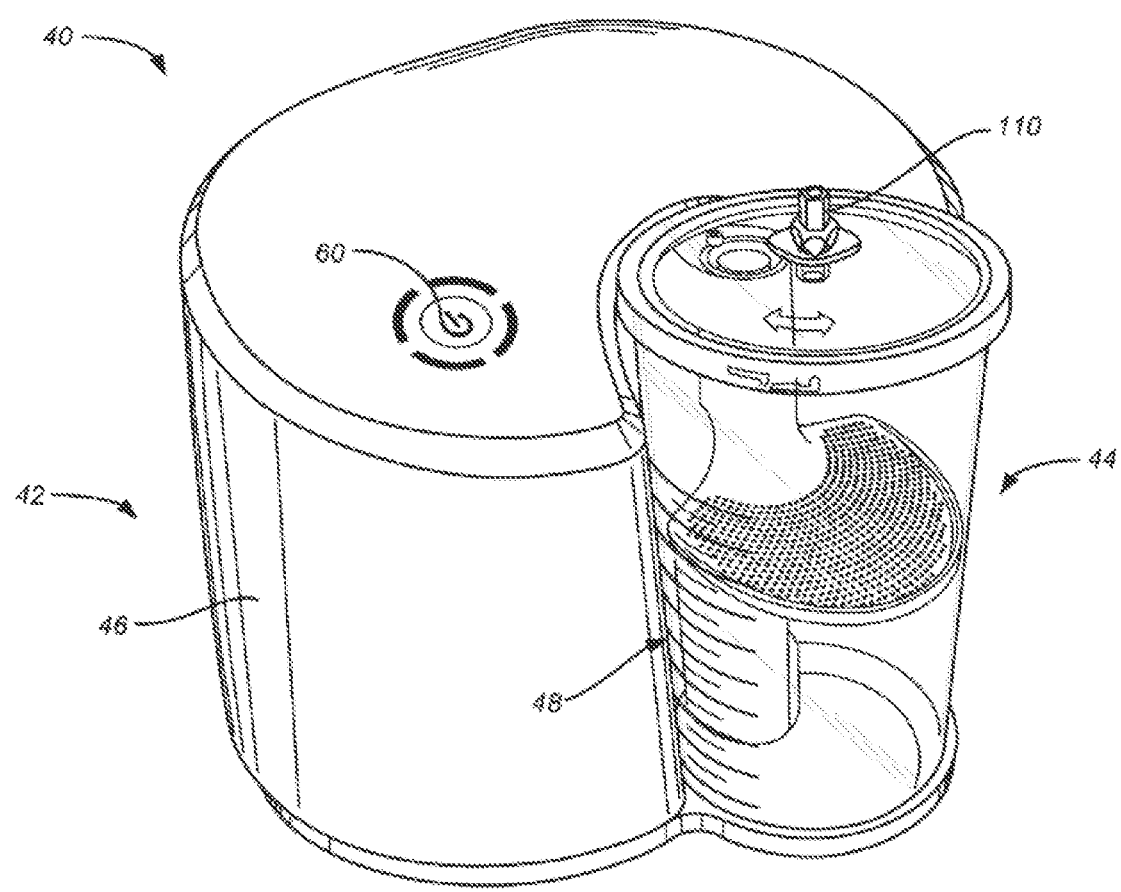
FIG. 2 is a perspective view of a vacuum console and a blood and clot collection canister with the collection canister received in a mounting region of the vacuum console.
Figure 3A:
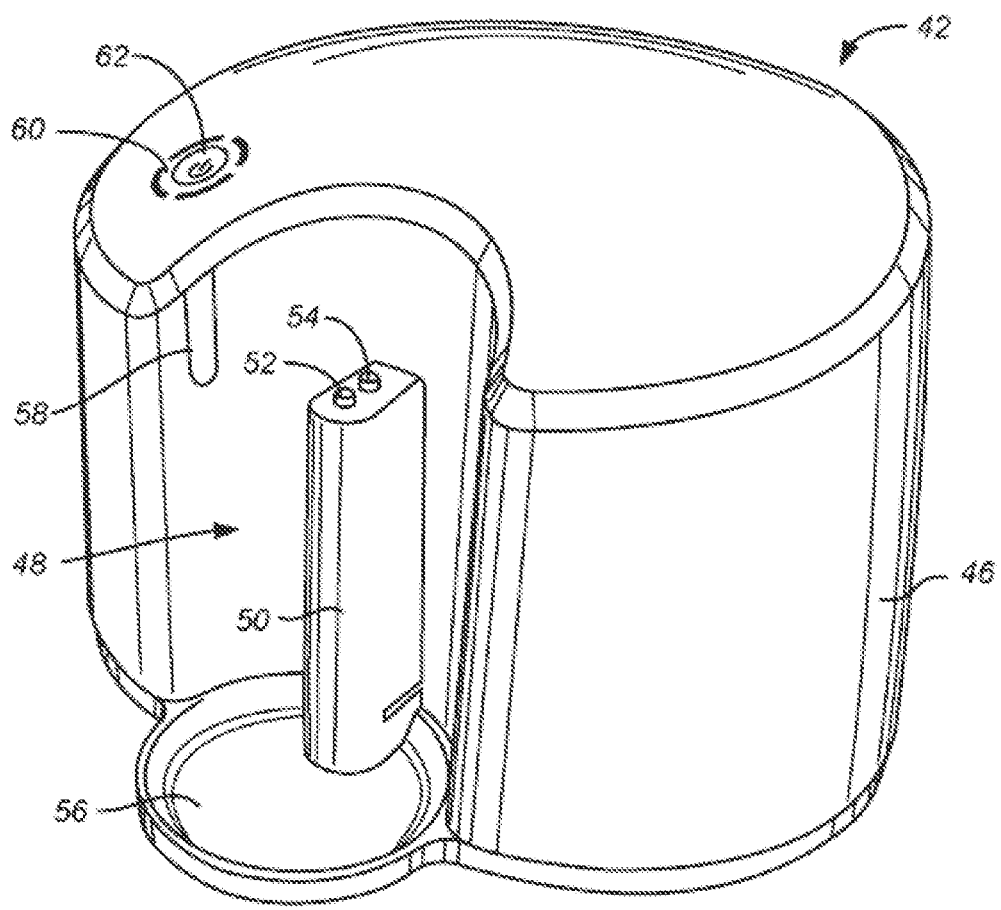
FIG. 3A is a view of the vacuum console of shown with the collection canister removed.
Figure 3B:
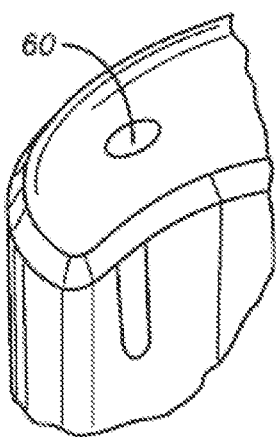
FIG. 3B is a detailed view of the on-off switch and a vacuum display region on a top surface of the vacuum console of FIG. 3, shown with the power off.
Figure 3C:
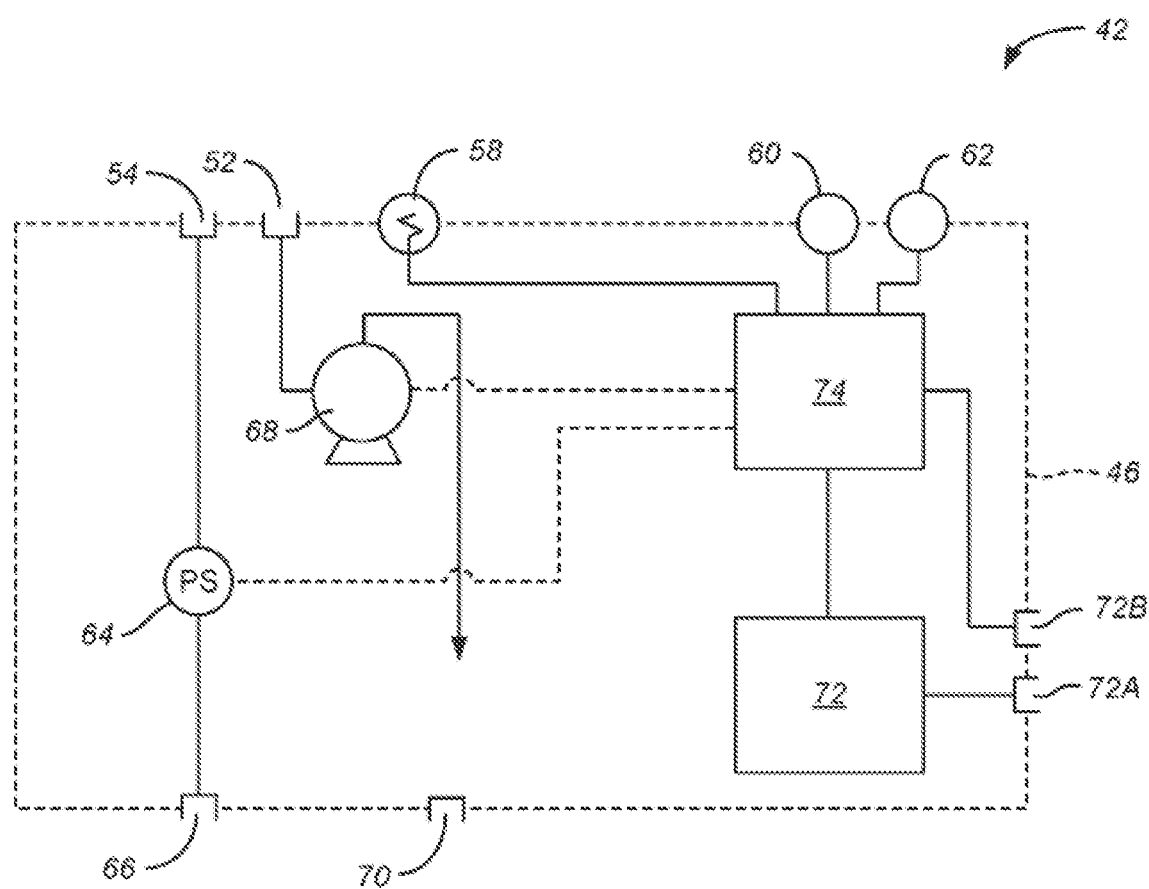
FIG. 3C is a schematic representation of the internal components of the vacuum console of FIGS. 1 to 3A.

Referring to FIGS. 3A-3C, the vacuum console 42 is shown with the vacuum canister 44 removed. A post 50 which forms a contiguous portion of the outer surface or wall of the enclosure 46 is formed within the recess 48 and extends upwardly from a bottom plate 56 which acts as a support for the collection canister 44 when it is received within the recess. A vacuum connector 52 and a pressure sensing connector 54 are formed in or on an upper surface of the post 50 and are located so that they will align with a pressure sensing port 104 and a vacuum port 102 (FIG. 5) on the vacuum canister 44 when it is received within the recess 48. One light 58 is located on a wall surface of the enclosure 44 within the recess 48 and is located so that it will illuminate the contents of the collection canister 44 when the system is in use. A second light (not visible in in FIG. 3A) is present on the opposite wall of the recess 48. The vacuum console 42 also has an on-off switch 60 on its upper surface. The on-off switch 60 illuminates when it is on (as shown in FIGS. 2 and 3A) and is not illuminated when the system is off (FIG. 3B). Additionally, a pressure display 62 is provided on the upper surface of the enclosure 46. As shown in FIGS. 2 and 3A, the display may be a circular light, e.g. having four segments which are sequentially illuminated as the vacuum level within the canister increases. Each quadrant represents the measured vacuum as a percentage of ambient pressure.

The internal components of the vacuum console 42 are schematically illustrated in FIG. 3C. The primary internal components of the vacuum console include a pressure sensor 64, a pump 68, a power supply 72, and a microprocessor controller 74. The pump 68 has an inlet connected to the vacuum connector 52 on the post 50 of the enclosure 46. Similarly, the pressure sensor 64 is connected to the pressure sensing connector 54 on the post 50. The pump can be turned on by the switch 60 and will draw vacuum through the connector 52 and release removed gas into an interior of the console. The console in turn is vented by a vent 70 on a bottom surface of the enclosure 46.

The functions of the pump will be controlled by the microprocessor controller 74, and the pressure output from sensor 64 will also go through the microprocessor controller 74. Each of the light 58, switch 60, and display 62 will be connected to the microprocessor controller 74 which is powered by the power supply 72. The power supply 72 is powered through line current connector 72A. The USB connector 72B is powered by microprocessor controller 74. The pump is plugged into an outlet via a power cord that is supplied with the pump. The power supply converts the AC current from the wall outlet to DC current which is what the microprocessor controller uses to power the pump, switch, lights, USB connector, etc.

In specific examples, pressure sensor 64 is connected to the microprocessor controller 74 and measures vacuum pressure in the canister through the pressure sensing connector 54. A second pressure sensor (not shown) is also connected to the microprocessor controller 74 and measures ambient pressure outside of the pump enclosure through an internal tube that is routed to a vent in the base of the pump. The microprocessor controller takes the vacuum pressure reading from the pressure sensor 64 and divides it by the ambient pressure reading from the second pressure sensor to calculate the vacuum pressure in the canister as a percent of ambient pressure.

Figure 4:
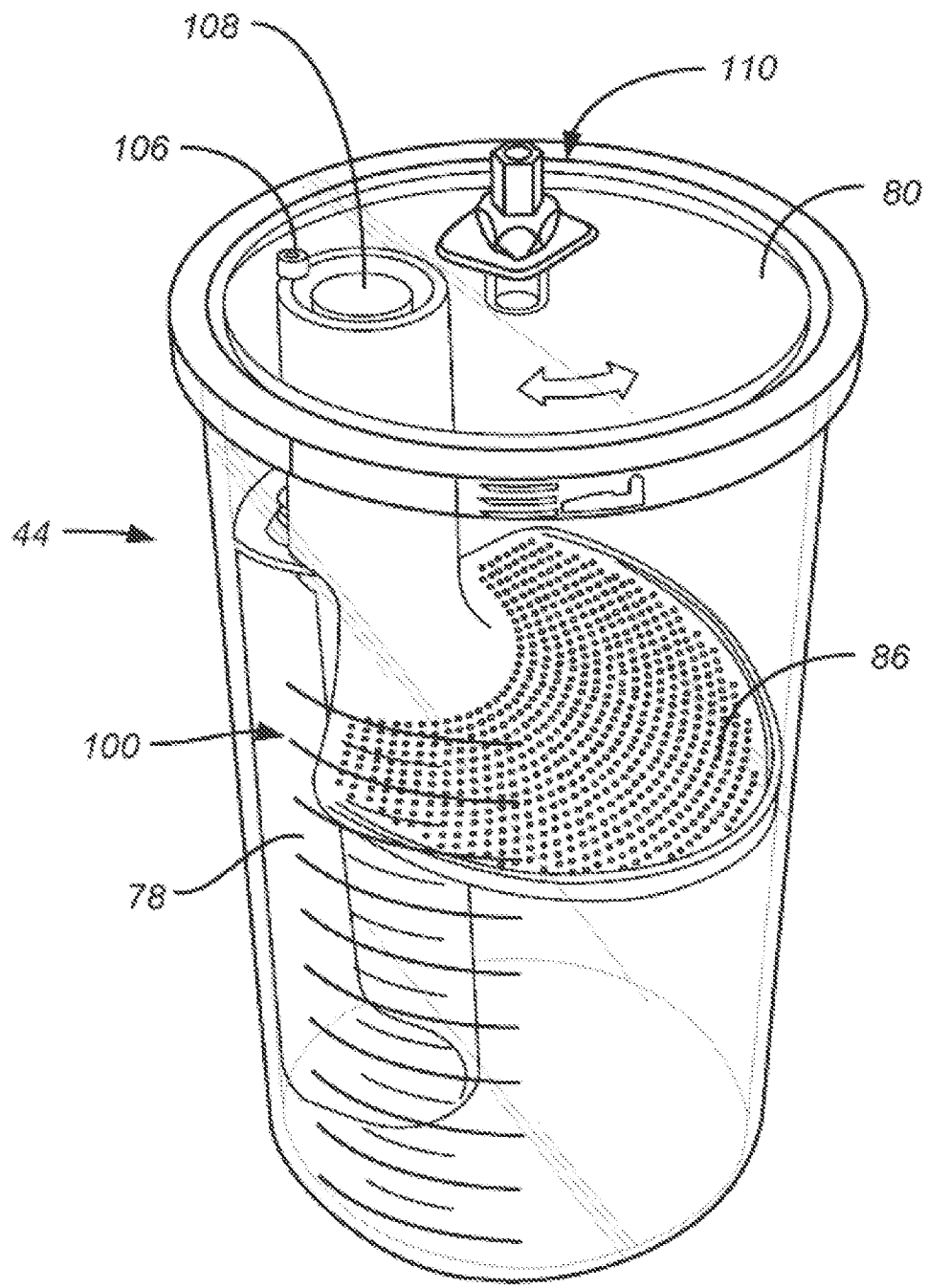
FIG. 4 illustrates a collection canister.
Figure 5:
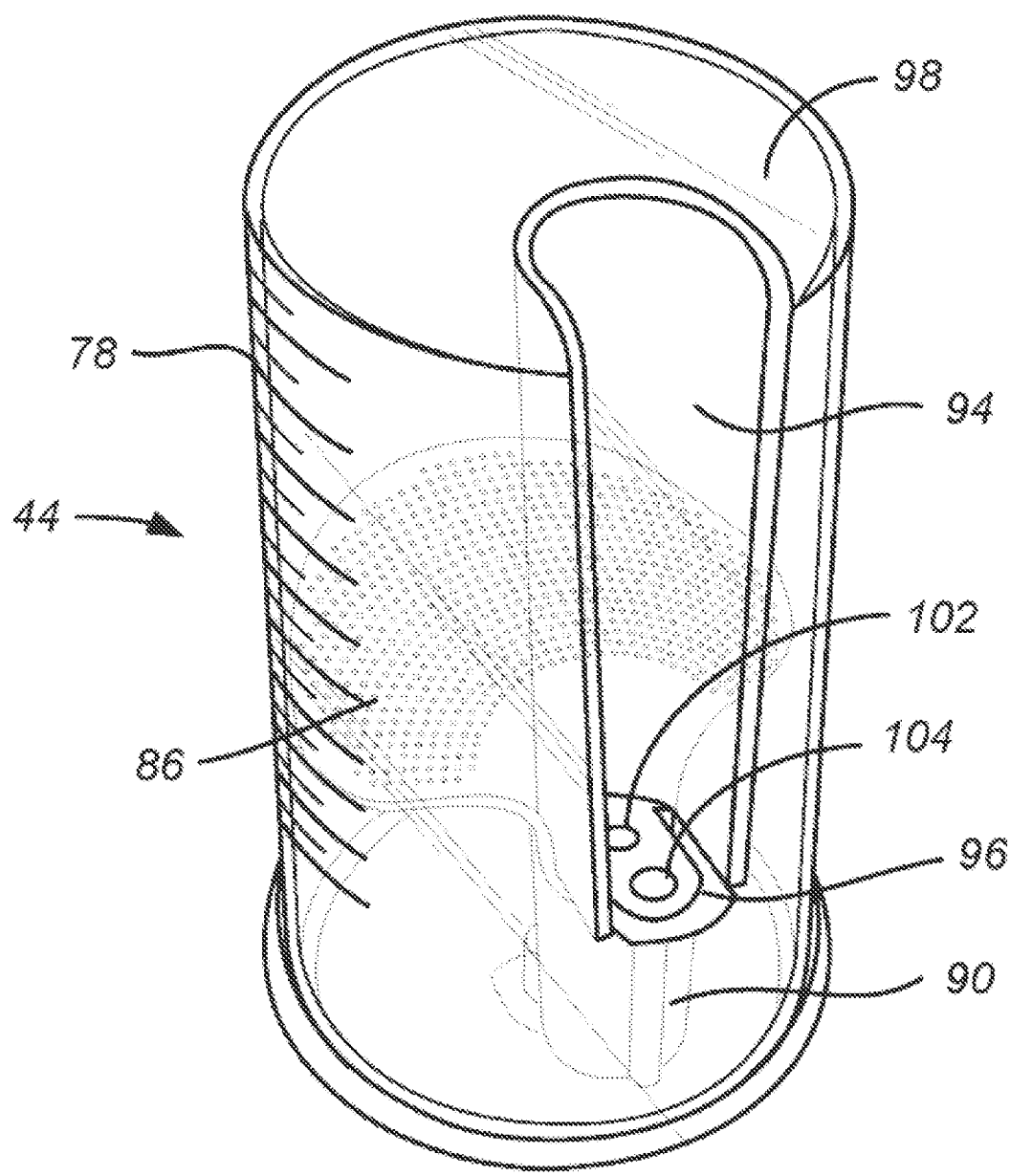
FIG. 5 illustrates the embodiment of the collection canister of FIG. 4, shown in an inverted or "upside down" view.
Figure 6:
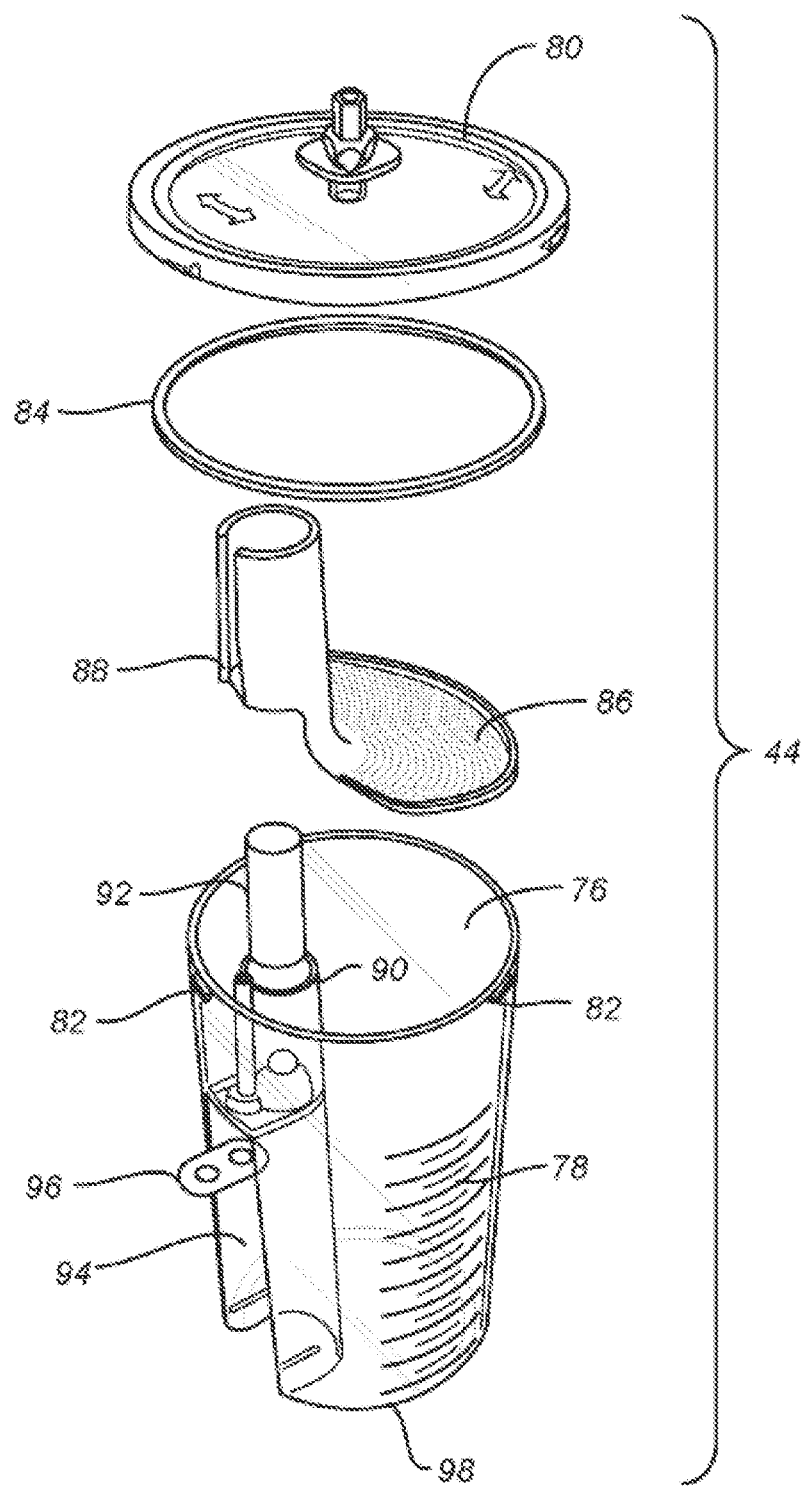
FIG. 6 is an exploded view of the vacuum canister of FIGS. 4 and 5.

Referring now to FIGS. 4-6, the collection canister 44 has a main body 78 which is typically formed from a polished, clear plastic material which is molded into the illustrated shape. The main body 78 has an open upper end 76 which can be covered by a removable clear plastic lid 80. The clear plastic lid 80 is typically attached by a bayonet connector 82, and a form or other gasket 84 will seal the lid to the open end of the main body 78.

A groove 94 is formed in one side of the main body 78 and is shaped so that it can be placed over the post 50 in the recess 48 of the enclosure 46 of the vacuum console 42. As best seen in FIG. 5, the pressure sensing port 104 and the vacuum port 102 are located at the upper end of the groove 94 so that they align and connect with the vacuum connector 52 and pressure sensing connector 54 on the post 50 when the canister 44 is in place in the recess 48.

The pressure sensing port 104 is connected to a tube or lumen which extends upwardly in the main body 48 of the canister 44 and terminates in an upper opening or aperture 106. Similarly, the vacuum port 102 extends upwardly through a much larger lumen or tube and terminates in an open aperture 108 at its upper end. The apertures 106 and 108 are located near the top of the interior of the main body 78 but will be below the bottom of the lid 80 when the lid is in place on the canister 44. Thus, both of the apertures 106 and 108 will be exposed to the interior of the canister 44 but will be maintained well above the mid-section and bottom where the clot and blood are collecting. In this way, the risk of contamination from blood and clot is minimized.

A filter plate 86, shown as a perforated screen but which could also be a woven screen or other separating member, is held in the mid-section of the interior of the main body 78 of the canister 44. The clot is drawn into the interior of the canister through a connector 110 which is attached to a proximal end of the catheter or other tubing. The clot and blood are drawn into the interior of the main body 78 by the vacuum which is drawn through the vacuum port 102 by the vacuum console 42, as previously described. As the clot and blood fall downwardly from connector 110 into the canister 44, the clot collects on the upper surface of the filter plate 86 while the blood flows through the perforations in the plate and collects in the bottom of the canister. As the plate is inclined downwardly from a sleeve 88 which is mounted on a post 90 in the interior of the canister, excess blood may flow over an open bypass region 100 (FIG. 4) which is formed on a backside of the plate and allows the blood to flow directly down to the bottom of the canister. Filter body 92 occupies the interior of post 90 and aperture 108 and prevents extracted material from contaminating the interior of enclosure 42. Filter body 92 occupies the interior of post 90 and extends to aperture 108. The filter body can thus prevent extracted material from contaminating the interior of enclosure 42. A groove 94 is formed on a side of the main body 78 of the canister 44 and is received over the post 50 in the recess 48 of the enclosure 46 in order to align the vacuum and pressure sensing connectors and vacuum ports. A gasket 96 is further provided at the seal between the vacuum ports and the vacuum connectors.

While the exemplary apparatus and methods for controlled clot aspiration described in FIGS. 7-19 may be used with the vacuum system 40, as just described, it will be appreciated that the inventions described and claimed herein are not limited to use with any particular vacuum console and instead are useful with any clot or other vascular thrombectomy or aspiration system including a thrombectomy or other vascular aspiration catheter in combination with a vacuum pump or other source where there is a risk of excess blood aspiration, clogging, or both.

Figure 7A:
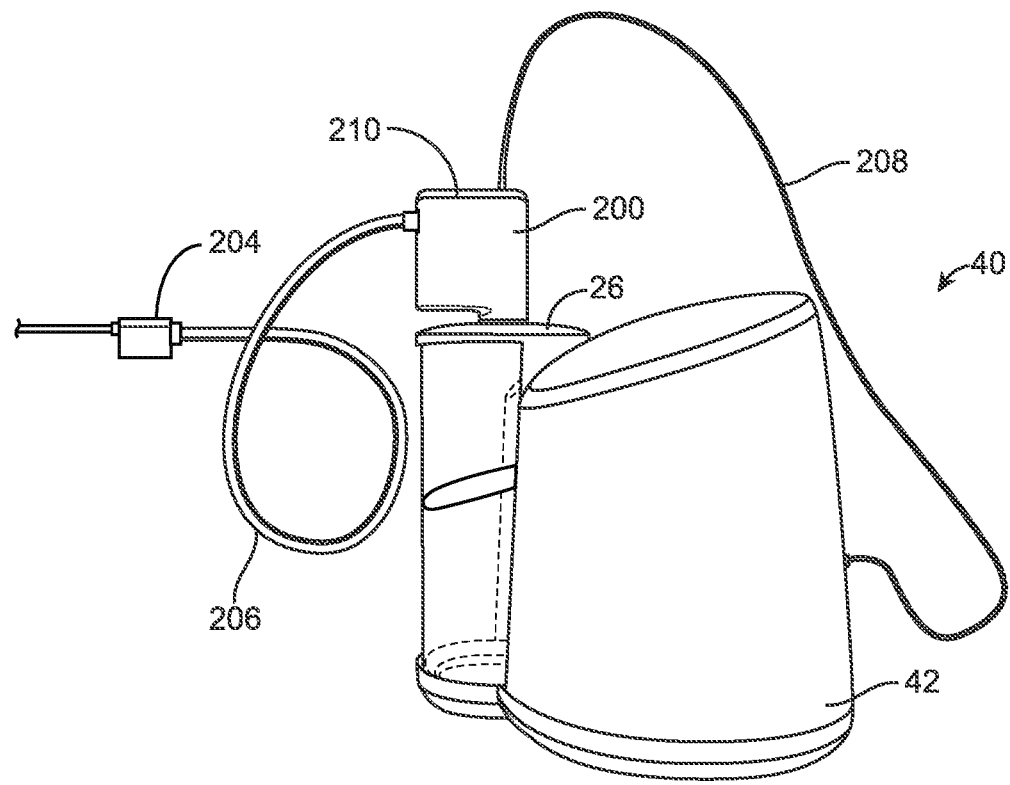
FIGS. 7A and 7B illustrate a vacuum console and collection canister, similar to those illustrated previously, having a vacuum aspiration control system attached thereto.
Figure 7B:
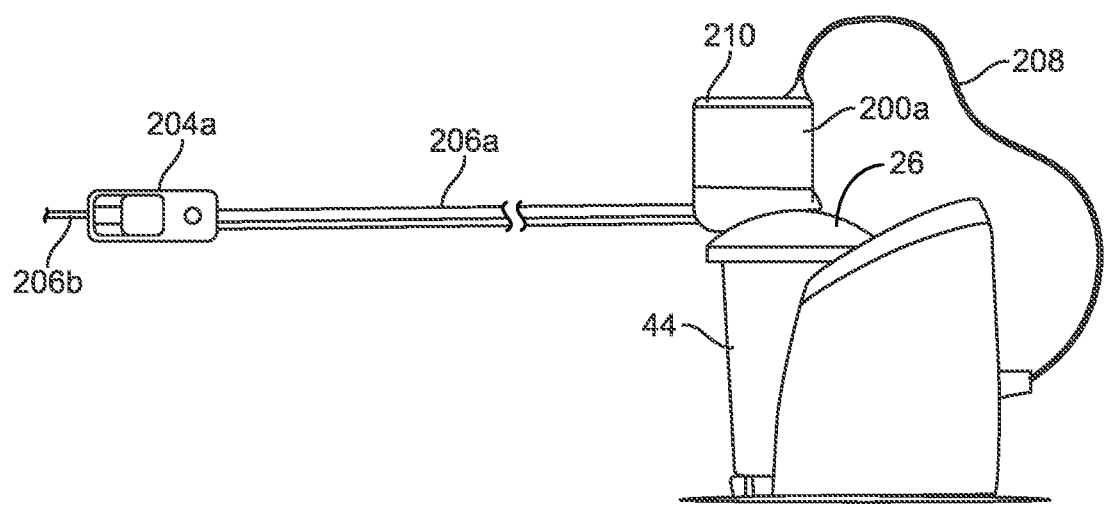

FIGS. 7A and 7B illustrate one example of an exemplary system 200 for performing controlled clot aspiration in accordance with the principles of the present invention comprises a base unit 210 and an external unit 204. A proximal end of a connecting tube 206 is connected to the base unit 210, and the external unit is secured on or to the connecting tube at a location spaced apart from the proximal end, typically by some distance sufficient to make conclusions about flow. The external unit 204 may be configured to connect directly to a hub or other proximal end of an aspiration catheter or may be configured to be connected in the middle of the connecting tube. The connecting tube is linear in an unconstrained configuration and flexible along its length.

The base unit 210 may be configured to sit directly atop the lid 26 on the collection canister 44 of the previously described vacuum console 40. Typically, a communication cable extends from the base unit 210 through a portion of connecting tubing 206 to a connection receptacle on the vacuum console 40 so that the base unit may be powered by the vacuum console and optionally can communicate data with the controller within the vacuum console.

Figure 8A:
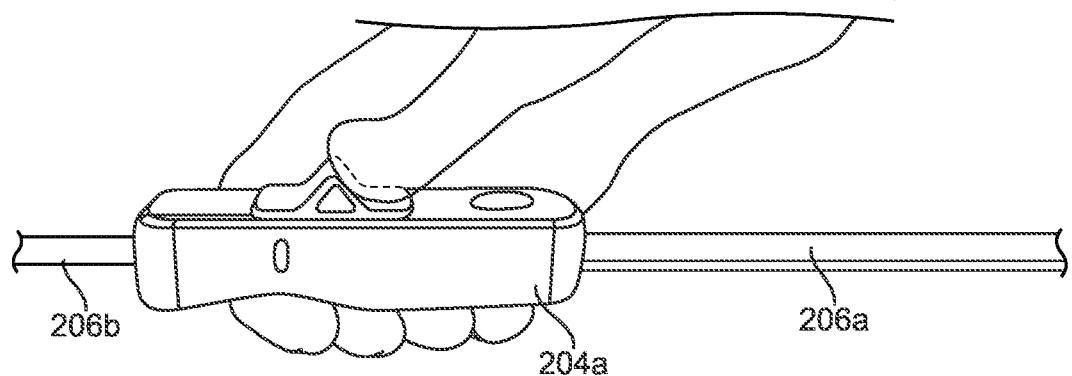
FIGS. 8A and 8B illustrate an external unit of the type suitable for use with the present invention.
Figure 8B:
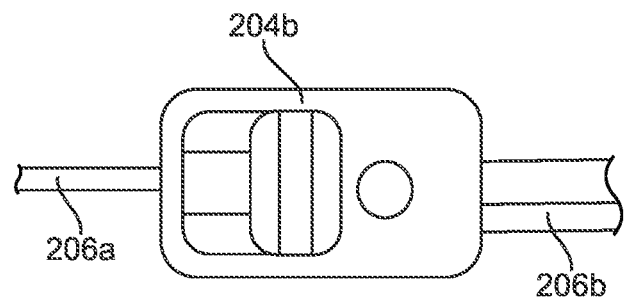

As shown in FIG. 7B, an external unit 204a may include a switch for initiating treatment using the vacuum console 40 and controlled clot aspiration system 200. The switch may also turn off the system, thereby providing a manual override of the algorithm that ensures the system is off with no flow. When the switch is on, the system may immediately enter an algorithm mode where it decides to remain open, enter a sampling mode, or initiate an extraction cycle in response to pressure sensor readings. Further details of the external unit 204a are shown in FIGS. 8A and 8B.

Figure 9:
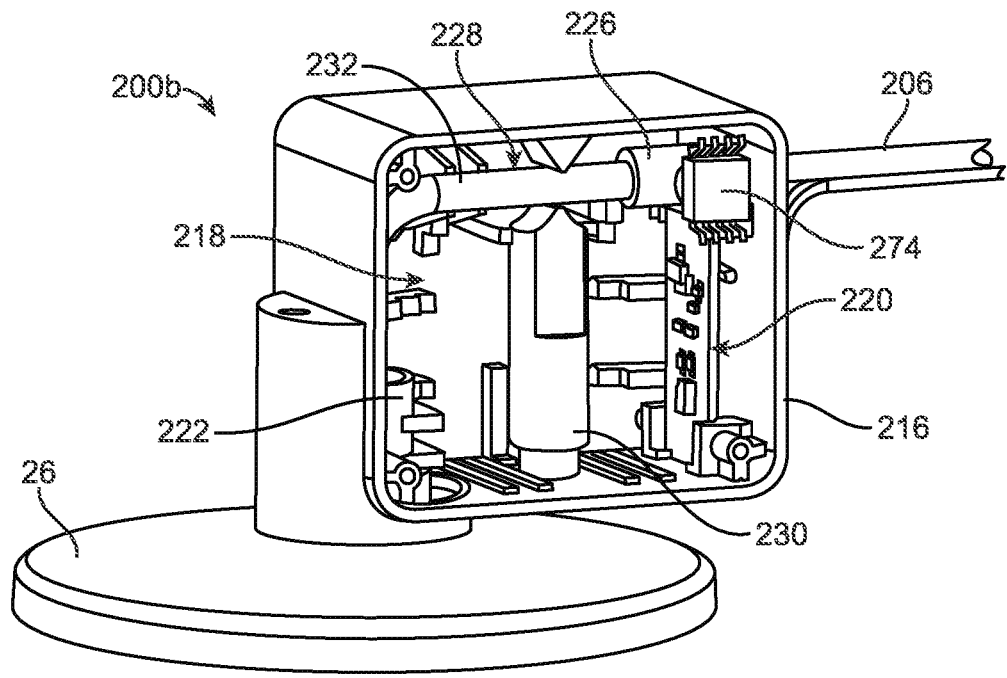
FIG. 9 illustrates an exemplary base unit enclosing an on-off valve and a controller of the type suitable for use in the vacuum aspiration control system, shown in section.

Referring now to FIG. 9, an exemplary base unit 200b may comprise a base unit enclosure 216 having an open interior cavity 218 which receives a number of components. For example, a controller 220, typically including a microprocessor on a printed circuit board, may be mounted within the cavity 218 together with a pressure sensor 224 secured between a tube segment 228 and a proximal end on the connecting tube 206 by a pressure fitting 226. The tube segment 232 may be collapsible and positioned in a pinch valve 228 which is driven by a solenoid 230. Pinch valve 228 may be biased into a closed position by a compressive spring (not visible), unless it is opened by solenoid 230. The base unit 200b further includes a connecting fitting 222 which is configured to be removably secured to a vacuum fitting (not shown) on the lid 26 of the canister 44. The controller 220 is configured to open and close the pinch valve 228 to allow and prevent, respectively, the flow of clot and blood through the tubing segment 232 from the aspiration catheter into the collection canister. Optionally, base unit 200b may include a button (not pictured) in electronic communication with printed circuit board 220, for advanced user control of various parameters of the system. In further embodiments, a base unit of the present invention may house or be in communication with a pressure chamber, a fluid source, additional on-off valves, or some such combination.

Figure 10:
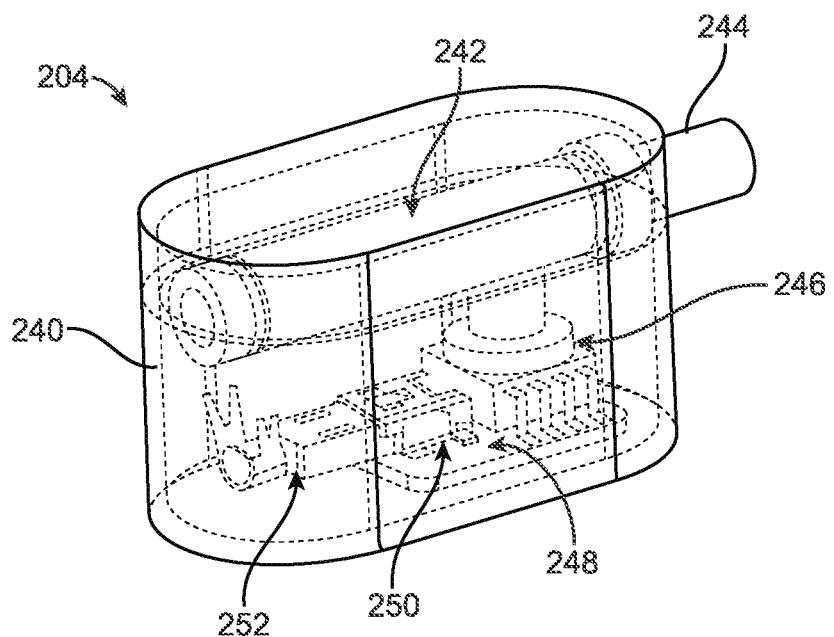
FIG. 10 illustrates an exemplary external unit showing internal components including a fitting and a pressure sensor, shown in phantom.

Referring now to FIG. 10, an exemplary external unit 204 includes an external unit enclosure 240 having a flow fitting 242 in an interior cavity thereof. The flow fitting 242 may be connected to portions 206a and 206b of the connecting tubing 206, as shown for example in FIGS. 7B, 8A and 8B. A second pressure sensor 246 may be mounted on a printed circuit board 248 and also within an internal cavity of the enclosure 240, and the output of the pressure sensor may be delivered to the controller 220 via a connective cable (not shown) which may be connected via a signal/power connector 250 and a mating signal-power connector 252, which may be a conventional USB port and plug. The connecting cable 206 may have dual lumens, as shown for example in FIG. 9, where one of the lumens can be used to route a communications cable between the external unit and the base unit, while the other lumen accommodates fluid flow. In further embodiments, an external unit of the present invention may house or be in communication with a pressure chamber, a fluid source, additional on-off valves, or some such combination.

By providing a first pressure sensor 224 in the base unit and a second, axially separated pressure sensor 246 in the external unit 240, the material flow rate through the connecting tube can be calculated based upon measured differential pressure by the controller. The controller may analyze the pressure differentials and flow rate to determine the contents flowing through the aspiration catheter, connective tubing, or both.

In an exemplary embodiment, the controller characterizes the state of a catheter's contents as unrestricted flow, restricted flow, or clogged. In one example, a high pressure differential between spaced-apart pressure sensors indicates unrestricted flow that may be comprised of primarily healthy, clot-free blood, or blood free of vessel-obstructing clot. In some examples, healthy blood is blood with a low enough proportion of cross-linked fibrin such that it is not sufficiently integrated to cause ischemia or other similar vessel occlusions. Aspirating such healthy blood with full aspiration may result in excessive blood loss that may require the premature termination of the aspiration procedure. In another example, a variable and intermediate or low pressure differential indicates restricted flow that may be comprised of clot, occlusive material, and blood. Such flow may benefit from full aspiration. In another example, a small pressure differential or a pressure differential approaching zero indicates a clog. Such flow, or lack thereof, may benefit from an extraction cycle. The use of differential pressure for detecting increased flow and occlusions, however, is exemplary and other flow measurement and material property measurement techniques will be available within the scope of the present invention.

Figure 11:
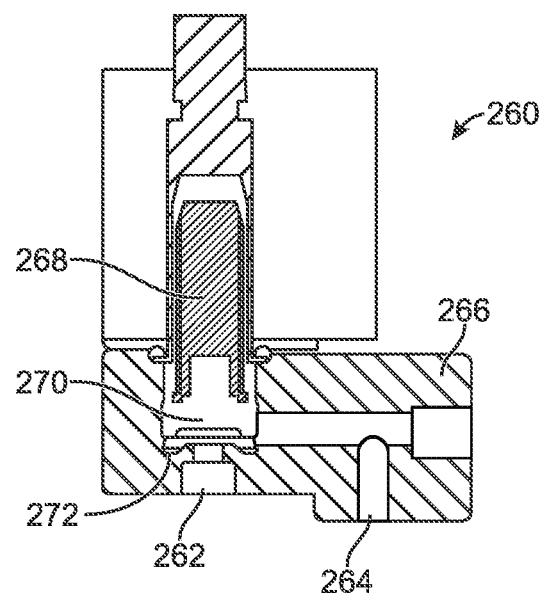
FIG. 11 illustrates an angle valve of the type which may be used as on-off valve in the present invention, shown in section.

Referring now to FIG. 11, instead of the pinch valve 228 shown in the base unit 200, an angle valve 260 may be employed. The angle valve has a connector 262 for being secured to a connector on the vacuum canister (not illustrated) as well as a fitting 266 that may be connected to the connecting tubing 206 which is in turn connected to the aspiration catheter. A solenoid 268 is typically present to open and close valve stem 270 and valve seat 272. In one example, the valves of the present invention open to permit aspiration and close to block aspiration. Alternatively, the valves of the present invention may open to allow fluid to enter the aspiration tubing and/or aspiration catheter and close to block the fluid.

Figure 12:
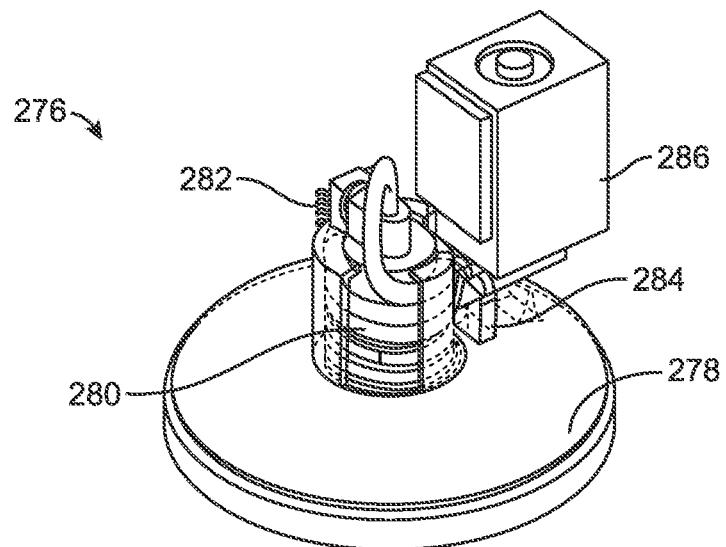
FIG. 12 is an isometric view of an angle valve connected to a coiled tube having pressure sensors at each end thereof mounted on a canister top.

Referring now to FIG. 12, the pressure sensors may be integrated into a single base unit 276 which may be fixedly attached to a canister cap 278. In this example, a first pressure sensor 282 and a second pressure sensor 284 are attached to opposite ends of a coiled flow tube 280 so that differential pressure may be measured. An angled valve 286 may be secured directly to an outlet of the coiled flow tube 280 in order to provide for the desired on/off flow control.

The controller 220 in base unit 200 may implement an algorithm that receives and analyzes pressure sensor data to open and close the on-off valve, e.g. a pinch valve 228 (FIG. 9) or an angle valve 286 (FIG. 12) or 260 (FIG. 11). The algorithm receives and analyzes the pressure data input hundreds of times per second. The data are compiled to determine the diameter of the attached catheter, determine the contents flowing through the catheter and aspiration tubing, and to determine the flow rate.

In one embodiment, the controller 220 implements an algorithm that uses pressure sensor data to analyze the contents flowing through an aspiration catheter and characterizes it as unrestricted flow, restricted flow, or clogged. A catheter with unrestricted is aspirating primarily healthy, clot-free blood, or blood free of vessel-obstructing clot. A catheter with mixed flow is aspirating a combination of clot, occlusive material, and blood. A catheter with little to no flow is clogged or occluded. If the algorithm determines that an excessive amount of blood is being aspirated, as is often the case for a catheter with unrestricted flow, it may restrict aspiration to reduce blood loss. If the algorithm determines that a catheter has restricted flow, it will typically allow full aspiration. If the algorithm determines that a catheter has little to no flow, it may initiate an extraction cycle to help remove any clogs or occlusions. As used herein, the term "clot" should be understood to encompass any occlusive material found in vasculature, such as thrombus, embolus, plaque, occlusive material, vessel blockage, or any other obstructive material. Clot references all such occlusive material for brevity's sake.

Figure 13:
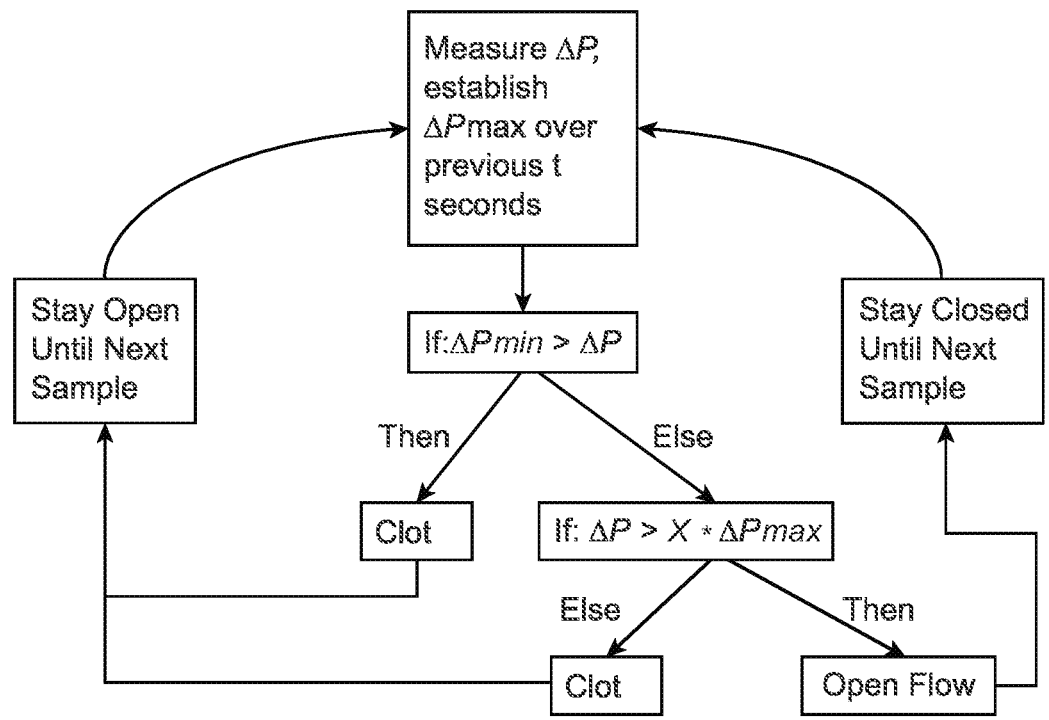
FIG. 13 illustrates an example of an algorithm suitable for use with the present invention.

FIG. 13 illustrates an example of an algorithm that uses pressure differentials ("ΔP") to determine flowrate and, based on the determined flowrate, controls the on-off valves of the present invention. In the illustrated algorithm logic tree, the first step is to measure max and minimum pressure differential windows over some assessment period and, after the assessment period, take an instantaneous pressure differential and compare it to these max and minimum pressure differential windows, which are incrementally updated. If the instantaneous pressure differential is lower than the minimum pressure differential of the assessment period, the algorithm determines that the system is in clot and instructs the system to continue full aspiration. On the other hand, if the instantaneous pressure differential is above the minimum pressure differential the algorithm determines whether the instantaneous pressure differential is above the product of the max pressure differential multiplied by a confidence interval, if it isn't the algorithm allows full aspiration, if it is the algorithm restricts aspiration to limit blood loss and enters a sampling state where aspiration is limited to brief surges to make new instantaneous pressure differential readings. In either case, whenever aspiration is allowed, the algorithm continually takes instantaneous pressure differential readings and compares them to the max and minimum pressure differentials collected throughout the procedure. In one example, when unrestricted flow (e.g. open flow) is detected the algorithm triggers a sampling state. In another example, when a clot is detected the algorithm initiates full aspiration or initiates an extraction cycle with pulsed aspiration.

In one embodiment, the present invention utilizes a correlation algorithm that determines whether a catheter has unrestricted flow, restricted flow, or is clogged, e.g. the catheter's state, based on a correlation between flow rate and such states. In another embodiment, the present invention utilizes a windowing algorithm that analyzes discreet portions of pressure sensor data to establish local minimum and local maximum pressure sensor readings. These windowed minimums and maximums are compared to a global maximum and global minimum across the data set. Given a sudden large delta in pressure readings, the system preferentially makes determinations of a catheter's state according to local minimums and local maximums. Pressure readings below minimums and above maximums signify a change in catheter state, e.g. below a minimum indicates a clogged catheter and above a maximum indicates an unrestricted flow state.

In an additional embodiment, the present invention utilizes an algorithm emphasizing an analysis of standard deviations across a discreet window of data points. The flow rate is compared to the average and mean flow rate. A small standard deviation indicates a catheter that is clogged or unrestricted, while a large standard deviation indicates a catheter that has restricted flow.

In one embodiment, a learning algorithm is used to determine the contents flowing through an aspiration catheter. Training data is formed by collecting pressure readings along the length of catheter in a variety of states, e.g. unrestricted flow, restricted flow, or clogged. Numerous pressure readings are recorded for each catheter state, and the algorithm then references those data sets to interpret never seen pressure readings to predict what state the catheter is in.

In another embodiment, the present invention utilizes an artificial neural network (ANN) that employs a multinomial logistic regression algorithm. The ANN is trained to predict answers by considering numerous training data sets. The training data includes both observed data as inputs and the actual outputs. The inputs are propagated across the ANN, which is comprised of layered nodes that each represent a linear transformation within the solution space. The ANN then "learns" by analyzing the difference between the ANN's calculated output and the actual output. This difference is translated into an error function. The error function is backpropagated across the ANN, whereby the weight of each node is modified according to its contribution to the error function. Weighting is a process of mathematical optimization that establishes which nodes optimally map inputs to their correct outputs. Numerous sets of training data are propagated across the ANN iteratively until the error function reaches convergence, i.e. some acceptable level of tolerance. Once the nodes have been properly weighted, in that the error function has reached convergence, the ANN can accurately predict the output of previously unseen input. Here, that means that the learned ANN can take novel pressure sensor data inputs and accurately predict catheter size and whether a catheter's contents should be classified as unrestricted, restricted, or clogged.

In some embodiments, the algorithm employs semi-supervised and unsupervised learning to continually update node weights. The algorithm may employ clustering, dimensionality reduction, and reinforcement learning to further improve prediction accuracy. In preferred embodiments, the algorithm can accurately interpret pressure fluctuations associated with switching between catheters of different diameters and filter out pressure fluctuations generated by manual movements of a separator within the aspiration catheter by determining and accounting for the cadence of the movement. Additionally, the present invention may employ an algorithm that uses a combination of the above algorithmic flow analysis techniques.

The algorithm may initiate a sampling mode when unrestricted flow is detected. In exemplary embodiments, the algorithm can detect a change in flow indicating unrestricted flow within milliseconds. In one embodiment of the sampling mode, the algorithm will cycle off aspiration and then open and close the on-off valve at a predetermined frequency. The sampling state conducts an aspiration surge when the valve is briefly opened and makes an assessment of the pressure sensor readings. Based on this aspiration surge, the algorithm determines whether the system should revert to full aspiration, with the on-off valve in the open position or remain in the sampling state. These sampling surges occur over a millisecond order of magnitude and ensure that full aspiration occurs only when the system is engaging clot and thus minimizes blood loss.

In an alternative embodiment, the system is powered on and has a brief delay before the algorithm assesses flow in the aspiration tubing. If the sensors indicate unrestricted flow, then an appropriate delay of time is calculated for which the on-off valve remains shut. After this delay, the on-off valve opens to briefly allow aspiration and take a pressure reading sample in the aspiration tubing to assess whether the system still has unrestricted flow or if it has been positioned into clot or other occlusive material. If the sampling detects unrestricted flow, a new delay is calculated (in some instances, incrementally longer for each consecutive reading up to a threshold). If the sampling detects clot, e.g. restricted flow or a clog, an appropriate delay of time is calculated for which the valve remains open. While open, the system assesses pressure sensors readings at a regular frequency to determine whether the system has been positioned such to cause unrestricted flow. These processes repeat until the procedure is finished.

An extraction cycle may be useful to clear occlusions in an aspiration catheter or to facilitate the aspiration of clot that are large or otherwise hard to aspirate. An extraction cycle establishes pressure differentials between the aspiration catheter and the vacuum source to generate pressure pulses. In general, these pressure pulses can employ multiple mechanisms to facilitate thrombus ingestion into an aspiration catheter. In one mechanism, the pressure pulse introduces an acceleration component that facilitates the extraction of occlusive material. In another mechanism, the pressure pulse creates a force impulse that breaks static friction momentarily, allowing a lower dynamic friction to ingest thrombus. In yet another mechanism, the pressure pulse moves the thrombus away from the distal tip of the catheter and subsequently rapidly forces contact between the thrombus and the catheter, macerating the thrombus.

In one example, an extraction cycle alternates between providing vacuum aspiration and relative positive pressure. An extraction cycle is typically initiated when an aspiration catheter is already under full vacuum. When an extraction cycle is initiated, the vacuum on-off valve between the catheter and the aspiration source is closed and the pressure in the aspiration catheter is increased, which may cause a positive pressure pulse and establish a pressure differential between the vacuum source and the catheter. When the on-off valve is then opened, the contents and the distal tip of the aspiration catheter experience the pressure differential as a negative pressure pulse that negatively impacts the structural integrity of any occlusions to a degree that a static force could only achieve with a greater supply of energy. The amplitude, or magnitude, of these pressure pulses are directly correlated to the pressure differential between an evacuated catheter and a pressure source (for positive pressure pulses) and a pressurized catheter and a vacuum source (for negative pressure pulses). The frequency with which the on-off valve opens and closes may be predetermined or responsive to pressure sensor data. An extraction cycle's pressure pulses may have an amplitude and frequency optimized to extract thrombus and similar occlusions from vasculature.

Pressure differentials in a catheter may be generated in a number of ways. In one example, pressure is generated by simply closing off a catheter's access to the vacuum source. In another example, pressure is generated by introducing fluid into the catheter, where the fluid is at a pressure between full vacuum and ambient pressure, at ambient pressure, at systolic pressure, or above systolic pressure (FIGS. 14-17). In another example, pressure differentials are generated by mechanical displacement of a pressure chamber (FIG. 18).

An extraction cycle may be automatically initiated when an algorithm of the controller 220 detects a clogged catheter, an occluded catheter, or a catheter positioned in clot. A catheter may be identified as in clogged state when the pressure differentials approach zero. In one example, the controller automatically initiates an extraction cycle after the system has detected a clog lasting for more than 5 seconds. Alternatively, an extraction cycle is initiated, or terminated, on demand by a user. An extraction cycle may provide pressure pulses for a predetermined time period. Alternatively, an extraction cycle assesses pressure sensor data each time the on-off valve opens to assess flow and to determine whether the extraction cycle should continue or end. If an extraction cycle has trouble clearing a clog, it may vary the amplitude and frequency of the pressure pulses. In one example, an algorithm on the controller 220 consults a library of different pressure pulses and chooses from among the library. If a specific amplitude and frequency starts to clear the clog, the algorithm may continue to generate pressure pulses of that frequency and amplitude until the clog is cleared.

Figure 14:
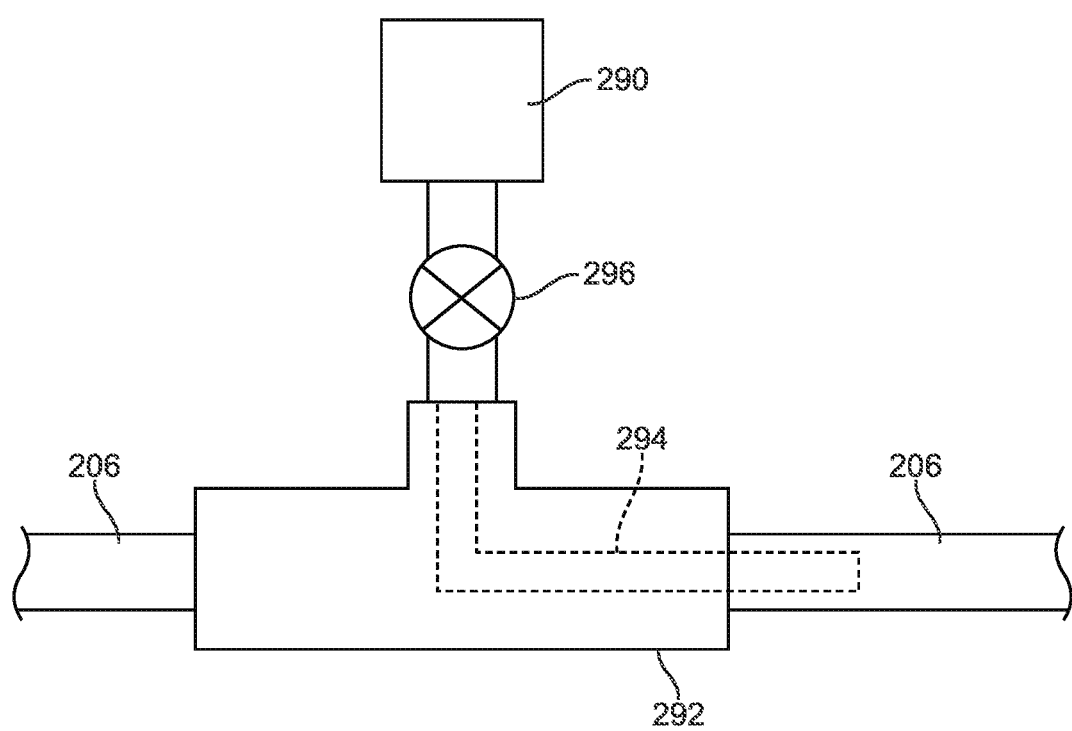
FIGS. 14-18 illustrate exemplary pulsed fluid injection assemblies suitable for use in the present invention.

FIG. 14 illustrates an example of a fluid system that may be used to generate pressure differentials, and thus pressure pulses. In this example, a fluid introduction unit 290 is attached along a length of the connection tubing 206 with a three-point junction 292. The three-point junction 292 may be positioned between the base unit 210 and the external unit 204 or may be positioned distal to both the base unit 210 and the external unit 204—i.e. in close proximity to an attached aspiration catheter. A fluid injection on-off valve 296 controls the flow of fluid (either liquid or gas) to inject pulses of pressure into the clot flow path that may facilitate the extraction of clot or other occlusive substances. In some instances, the flow of fluid is introduced directly into the connection tubing 206. In other instances, the flow of fluid first traverses an injection tube 294 before entering the connection tubing 206. The injection tubing 294 may direct the pressure pulse towards the catheter, which may optimize the pressure pulse. In one example, the three-pint junction 292 has a T-joint structure as illustrated in FIG. 13. Alternatively, a three-point junction may have a Y-joint structure (not illustrated). The Y-joint may beneficially direct fluid from the fluid introduction unit towards the catheter, which may optimize the pressure pulse in a similar manner to the injection tubing of the prior example.

Figure 15:
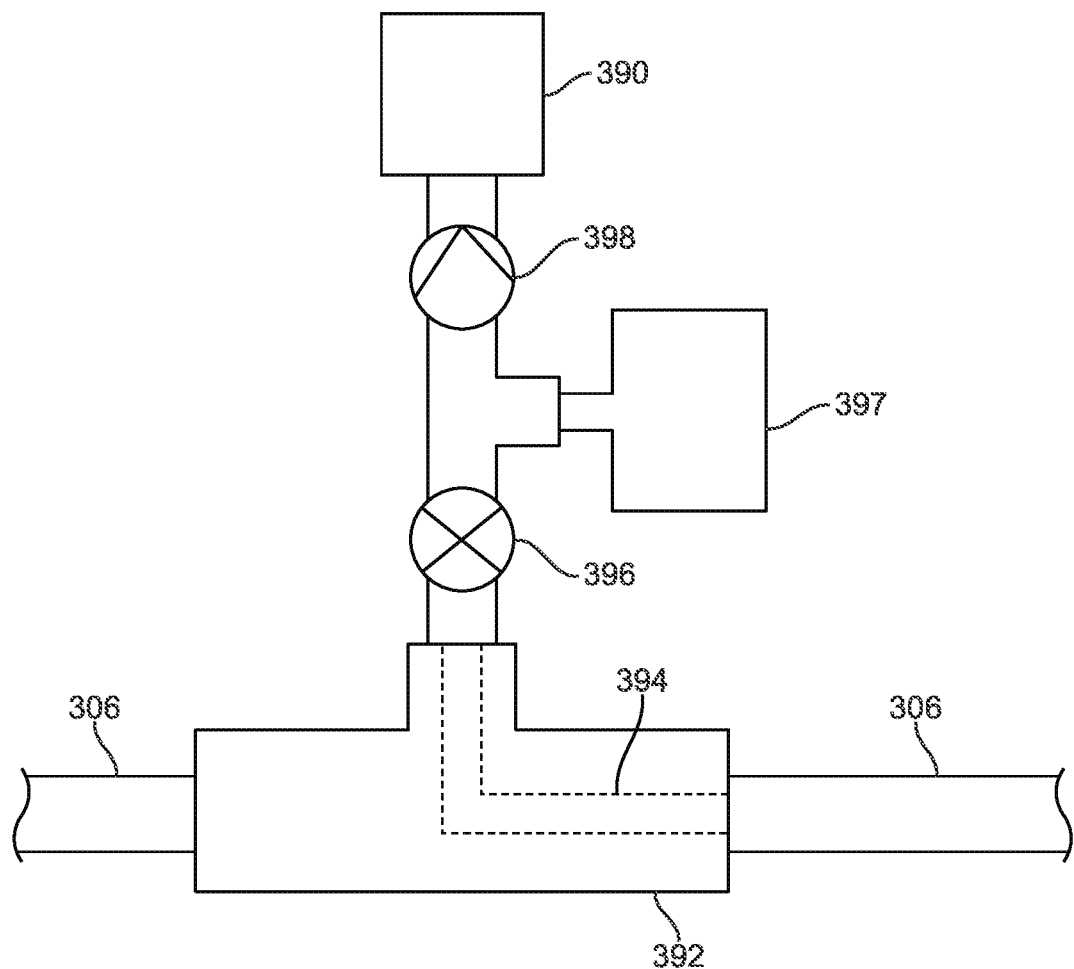

FIG. 15 illustrates an alternative fluid system that uses a pump 398 that may be connected between a fluid reservoir 390 and an injection valve 396. In one embodiment, the pump 398 cycles on when the injection valve 396 opens. The pump provides work by forcefully injecting fluid from a fluid reservoir 390, through the injection on-off valve 396, into an injection tube 394 and/or connection tubing 306. In this example, the magnitude of the positive pulse of pressure is directly correlated to the throughput (e.g. size) of the pump 398. In a second embodiment, a pressure chamber 397 is positioned between the pump 398 and the injection valve 396. A pressure chamber 397 allows the pump 398 to provide work even when the injection valve 396 is closed. While the injection valve 396 is closed, the pump 398 forcefully injects fluid from the reservoir 390 into the pressure chamber 397, whereby the pressure chamber 397 becomes pressurized. When the injection valve 396 opens, pressure is released from the pressure chamber 397 into the injection tube 394 and/or connection tubing 306. In this embodiment, since the pump 396 can build up pressure over time, the magnitude of the positive pulse of pressure is not directly correlated to the throughput (e.g. size) of the pump 398, thus this embodiment allows for a smaller pump. To provide even greater control over the duration or magnitude of positive pressure pulses, the opening and closing of the injection valve may be throttled or manipulated to modulate rate of injection. Additionally, a pressure sensor may be included in pressure chamber 297 to monitor and control the buildup of pressure.

Figure 16:
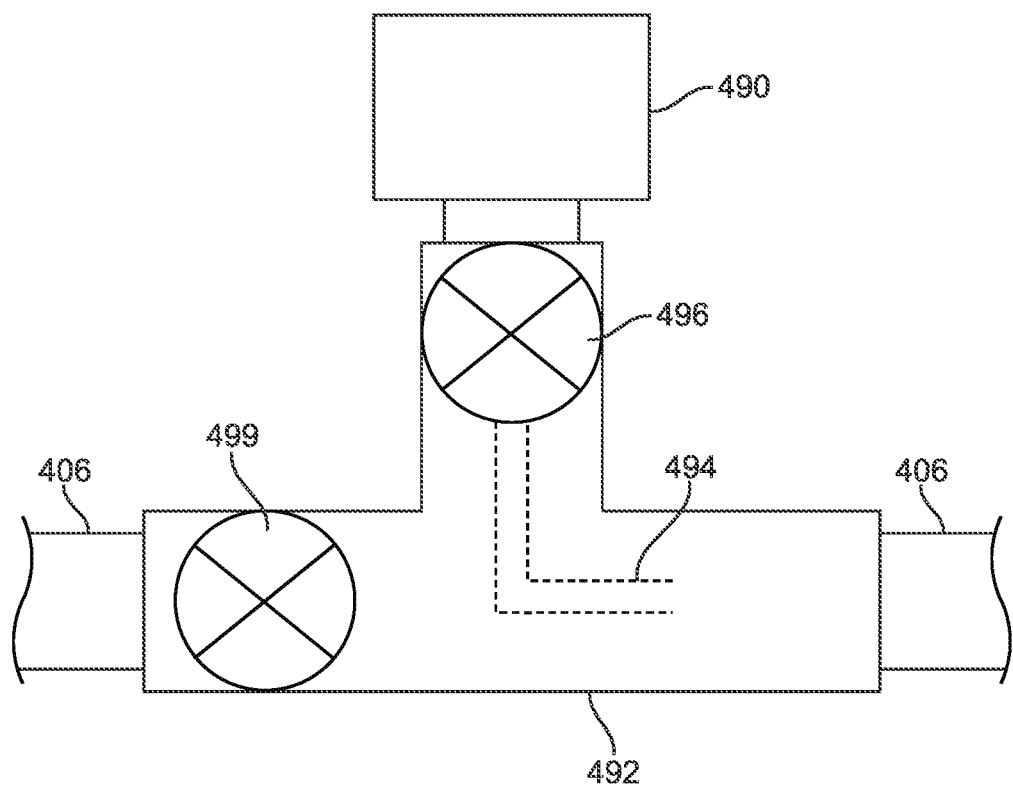

FIG. 16 illustrates another three-point junction 492 attached along connection tubing 406. The three-point junction 492 may be positioned between the base unit 210 and external unit 204 or may be positioned distal to both the base unit 210 and the external unit 204. A pressure valve 496 controls the generation of positive pulses of pressure from fluid chamber 490. Fluid from the fluid chamber 490 may flow directly into connection tubing 406 or may first traverse an injection tube 494 before entering the connection tubing 406. An aspiration valve 499 controls the application of vacuum aspiration from an attached vacuum source. In this embodiment, the three-point junction 492 has valves to control both vacuum forces and positive pressure pulses. This allows the three-point junction 492 to alternate between applying vacuum aspiration and pulses of pressure, wherein the pressure is above that of the vacuum source. The aspiration valve 499 and the pressure valve 496 may be opened alternatively, simultaneously, with a delay, or in some overlapping sequence. In one overlapping sequence, one valve starts to open when the other valve is starting to close, whereby there is a brief period where both valves are at least partially open. In other overlapping sequences, sometimes both valves are open and both valves are closed for at least short periods of time.

In one embodiment, an aspiration valve 499 is positioned between a catheter and an aspiration source to modulate aspiration and a pressure valve 496 is positioned between the catheter and fluid source to modulate fluid injection. The present invention may selectively open and close both aspiration valve 499 and pressure valve 496 to create pressure differentials within the catheter and/or aspiration tubing that result in pressure pulses of a desired amplitude and frequency.

Figure 17:
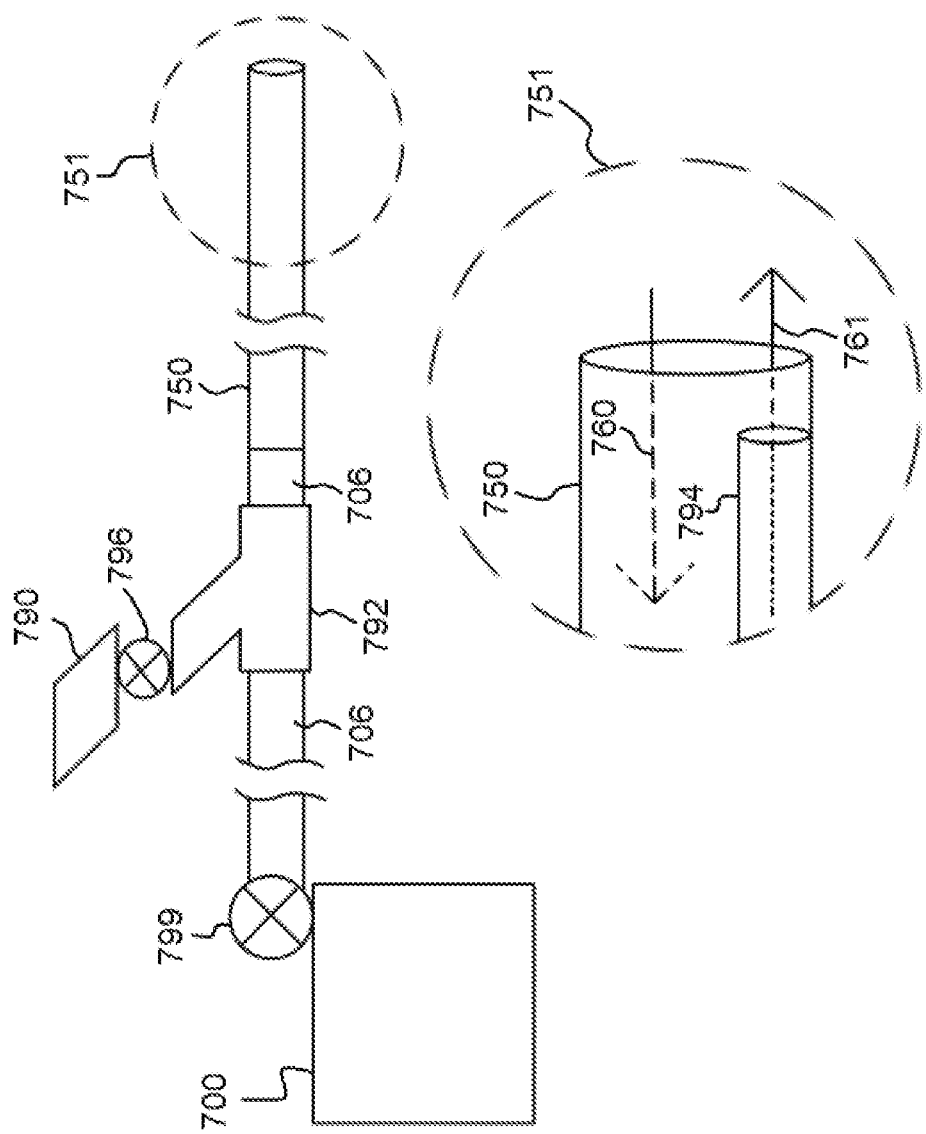
Figure 18:
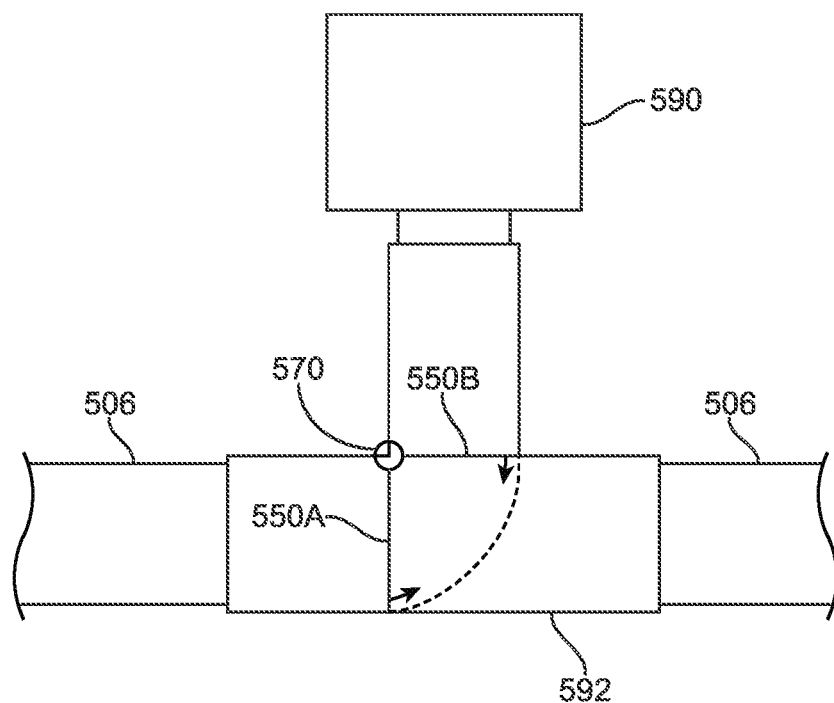

FIG. 17 provides a perspective view of a three-way joint and the components it connects. In this example, a connection tubing 706 acts as a common conduit between a vacuum source 700, a pressure source 790, and an aspiration catheter 750. The connection tubing 706 may have a first end configured to attach, or be placed in fluid communication with, the vacuum source and a second end configured to attach, or be placed in fluid communication with, the aspiration catheter. In one example, the second end is attached to the aspiration catheter with a rotating hemostasis valve. A three-way joint 792 may be positioned proximate to the second end to provide pulses of relative positive pressure near the aspiration catheter 750. In one example, the three-way joint 792 is an angled joint or Y-joint, whereby fluid from the pressure source is directed towards the aspiration catheter 750. In some examples, the three-way joint 792 includes injection tubing 794, which directs fluid from the pressure source towards the aspiration catheter 750. In some examples, the injection tubing 794 extends from the three-way joint into the aspiration catheter, whereby fluid flows from the pressure source into the aspiration catheter 750. In another example, the injection tubing 794 extends from the three-way joint to a position proximate a distal end of the aspiration catheter, as depicted in perspective 751, which provides a zoomed-in perspective of the distal end of the aspiration catheter 750. In this example, the pressure source may cause fluid to flow according to directional arrow 761 and the vacuum source may cause fluid to flow according to directional arrow 760. In some embodiments, the controller may modulate a vacuum valve 799 and a pressure valve 796, whereby the closing of the vacuum valve 799 and the opening of the pressure valve 796 may result in a relative increase in pressure at a distal tip of an aspiration catheter. Alternatively, the opening of the vacuum valve 799 and the closing of the pressure valve 796 may result in a relative decrease in pressure at the distal tip of the aspiration catheter 750. In some instances, these changes in pressure are transmitted along a length of the aspiration catheter as a pressure pulse. In some embodiments, a controller may close vacuum valve 799 and open pressure valve 796 for a small period of time, thus allowing a minimal volume of fluid from the pressure source 790 to be introduced into a proximal end of aspiration catheter 750 to increase the relative pressure at a distal end of the aspiration catheter 750 before reverting to vacuum by re-opening vacuum valve 799 and closing pressure valve 796. Similarly, a controller may close vacuum valve 799 and open pressure valve 796 for a longer period of time, allowing a larger volume of fluid from the pressure source 790 to be introduced into the aspiration catheter 750 to facilitate movement of obstructive material away from the distal end of aspiration catheter 751 before reverting to vacuum by re-opening vacuum valve 799 and closing pressure valve 796. In some embodiments, the connecting tubing 706 may have a dual lumen along a portion of its length, whereby one lumen accommodates fluid and a second lumen accommodates wiring, which enables the controller to modulate both the vacuum valve 799 and the pressure valve 796.

FIG. 18 illustrates another embodiment of a valve structure that controls both aspiration forces and positive pressure pulses. In this example, a three-point junction 592 attaches to connection tubing 506 and pressure chamber 590. A gate valve 550 translates at axis 570 to block aspiration in a 550A position and to block fluid introduction in a 550B position. The gate valve 550 may provide pulsed aspiration by oscillating back and forth at a predetermined or responsive frequency as controlled by an algorithm in the controller 220. In this example, the three-way gate valve exists at the juncture between the aspiration source, the pressure source, and the catheter. The gate valve 550 translates between blocking the aspiration source and blocking the pressure source to effect pressure pulses of a desired amplitude and frequency.

In an alternative embodiment, fluid injection does not occur at a three-point juncture, but rather occurs at a more distal region closer the catheter tip. The location of the relative pressure injection may be used to optimize the pressure pulse variation in order to facilitate clot removal. In one embodiment, a distal region of an aspiration catheter includes a valve that can be opened and closed, e.g. the distal valve. In one example, an aspiration valve is closed, and the distal valve is opened to allow blood to rush into the catheter, which increases the pressure in the catheter and amplifies the pressure differential between the catheter lumen and the vacuum source. Typically, the distal valve is then closed, and the aspiration valve is opened, wherein the pressure differential between the vacuum source and the catheter results in a pressure pulse. In another embodiment, fluid is transferred into an aspiration catheter from another adjacent catheter. For instance, an inner catheter may deliver fluid to an outer aspiration catheter. Alternatively, an outer catheter may deliver fluid to an inner aspiration catheter through a valve structure. In either case, the fluid is delivered along the length of the aspiration catheter, rather than through a proximal end. In a similar manner, an adjacent catheter may offer an additional connection to a vacuum source.

Figure 19:
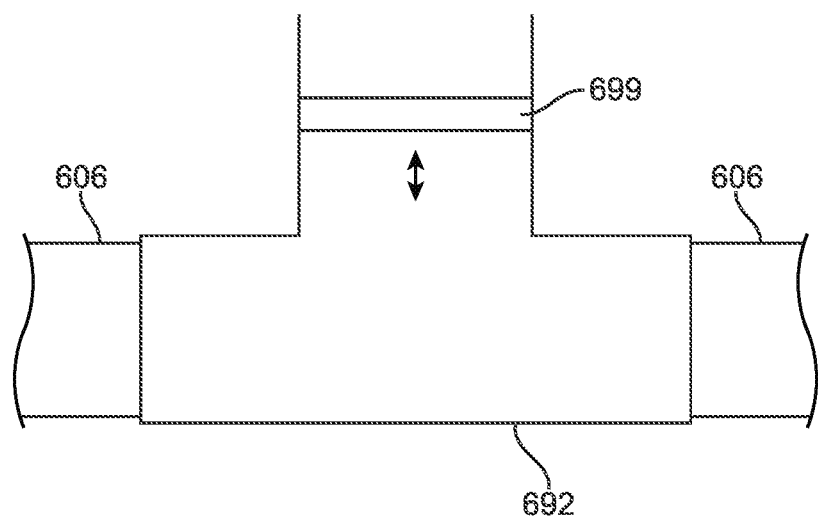
FIG. 19 illustrates a mechanical displacement assembly for manipulating pressure with the present invention.

FIG. 19 illustrates a mechanical assembly for generating pressure pulses. In this example a mechanical piston 699 can replace the previous embodiment's injection valves, pressure chambers, pumps, and fluid reservoirs. The stroke of the piston 699 or alternative mechanical device can be controlled to adjust the volume of the catheter resulting in the generation of negative pressure on one stroke and the generation of positive pressure on the other stroke. In general, a mechanical actuation device actuates back and forth to increase and decrease the overall volume of the system. When the device actuates to increase volume, pressure decreases, and when the device actuates to decreases volume, pressure increase. These pressure changes may create, amplify, or assist pressure pulses of an extraction cycle. The piston 699 may be provided in a three-point juncture 692 that attaches to connection tubing 606. Other mechanical means of controlling volume, or pressure, of the catheter include linear motors, stepper/servo motors, cam follower actuators, solenoids, audio exciters, voice coil actuators, diaphragms, peristaltic pumps, rotary vanes, gears, screws, syringes etc. (not pictured).

High frequency pressure pulses may be enabled by a mechanical method, such as that depicted in FIG. 19. To provide high frequency pressure pulses, a catheter must be rapidly pressurized and rapidly evacuated. The fluid injection systems of FIGS. 14-18 may readily provide a rapid influx of pressure; however, it may take a non-insignificant amount of time for the vacuum source to bring that catheter back to full vacuum. If the next influx of pressure occurs too early, the catheter will not have had time reach full vacuum, or near full vacuum. In this scenario, the pressure differential between the not-quite-evacuated catheter and the pressure source will be lower and the resulting pressure pulses will have a lower amplitude, which may be suboptimal in some scenarios. To avoid low amplitude pressure pulses caused by a high frequency, the present invention may utilize a vacuum recovery system to reduce the time required to return a catheter to full vacuum after an influx of positive pressure. With a vacuum recovery system, the present invention enables pressure pulses with both a high amplitude and a high frequency.

FIG. 19 illustrates a device that may function as a vacuum recovery system by generating pressure differentials. Alternatively, a vacuum recovery system may utilize a syringe, an evacuated chamber, a second aspiration pump, or some combination of these options. A syringe is a piston actuated device that retracts to increase a system's volume (and thus decrease pressure) and advances to decreases a system's volume (and thus increase pressure). A syringe-like device may beneficially assist not only vacuum recovery but also positive pressure pulse generation. In one example, a syringe is used during an extraction cycle. In such an example, a catheter starts at full vacuum. The vacuum source closes, the syringe advances (to reduce system volume), and, optionally, fluid is injected, which all facilitates the formation of a positive pressure pulse. Next, the vacuum source opens, and the syringe retracts (to increase system volume) to generate a negative pressure pulse, whereby the syringe speeds the catheter's return to near full vacuum. Alternatively, an aspiration pump is configured to selectively prime an evacuated chamber that is opened to the catheter, in addition to an aspiration pump, after each pressure pulse. Together, the aspiration pump and the evacuated chamber more rapidly return a catheter to full vacuum. While the aspiration pump is closed to the catheter, it may be opened to the evacuated chamber to further prime the evacuated chamber between pressure pulses. In a further alternative, a secondary aspiration pump assists a primary aspiration pump to facilitate vacuum recovery after each pressure pulse.

Figure 20:
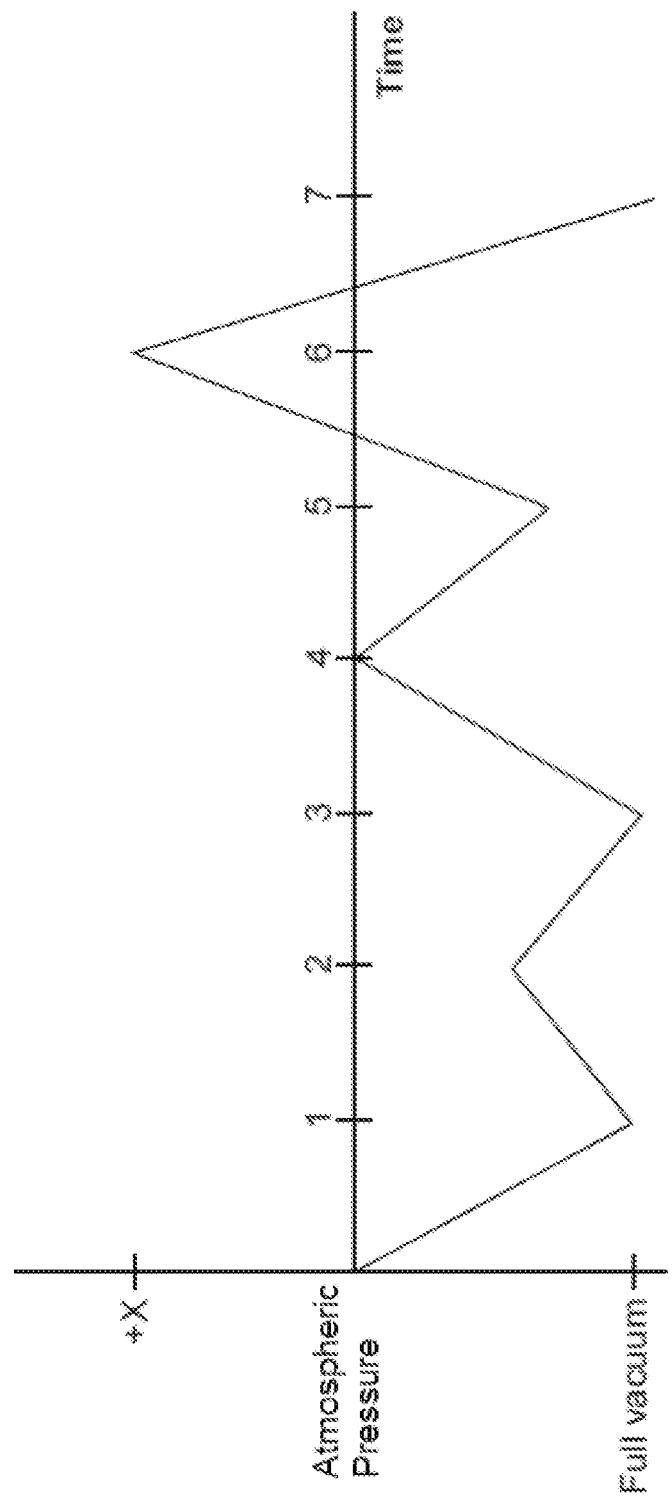
FIG. 20 illustrates a graphical representation of one embodiment of pulsed aspiration, where catheter internal pressure is varied over time.

FIG. 20 illustrates a graphical representation of an example pulsation protocol. An extraction cycle may use a pulsation protocol to systemically manipulate the amount of pressure within a catheter to facilitate the extraction of occlusive material. Pressure in a catheter may be manipulated by a variety of methods. For instance, vacuum aspiration may be used to reduce pressure within the catheter and the removal of vacuum suction and/or the introduction of fluid may be used to increase pressure within the catheter. In other instances, a mechanically actuating device may alternate between increasing and decreasing pressure within a catheter. In the example illustrated by FIG. 20, at time 0, the catheter has not been subjected to any suction forces and is at atmospheric pressure. From time 0 to time 1, the catheter has lost pressure, lunging from atmospheric pressure to near full vacuum (i.e. near −29.9 inHg). From time 1 to time 2, the catheter has gained pressure, which decreases vacuum strength. From time 2 to 3, the catheter has lost pressure, which returned the catheter to near full vacuum. From time 3 to 4, the catheter has gained pressure and returned to ambient pressure. From time 4 to 5, the catheter has lost pressure, again lunging from atmospheric pressure to near full vacuum. From time 5 to 6, the catheter has gained pressure, which caused the pressure to surge from near full vacuum to above ambient pressure. From time 6 to 7, the catheter has lost pressure, lunging from a pressurized state above atmospheric pressure to near full vacuum.

A pulsation protocol of the nature illustrated in FIG. 20 may be executed once or may be repeated several times. In alternative embodiments, the pulsation protocol may include additional time periods with additional pressure variations and pressure patterns. In general, the system's pressure may vary from between near vacuum to above average systolic pressure. The duration of the pulsation protocol may be predetermined or adaptive to pressure sensor readings. For instance, the controller may prolong or shorten a pulsation protocol based on pressure sensor readings. In some examples, the system may remain at a stable pressure state across one or more time periods. For instance, the controller may cause the system to dwell at near full vacuum. The dwell time in each pressure state and the frequency with which the system transitions between pressure states may be optimized to ingest different clot or occlusive material compositions. Although FIG. 20 illustrates a pulsation protocol with a stable and consistent frequency, in other examples the frequency of a pulsation protocol is variable or some combination of partially stable and partially variable. High amplitude (or high magnitude) pressure pulses may be generated by generating large pressure differentials. For instance, FIG. 20 illustrates a high amplitude pressure pulse between times 5 and 7. Lower magnitude pressure pulses may be generated by oscillating between less extreme high pressures and low pressures. For instance, the low end of the pressure pulse may not reach near full vacuum, the high end of the pressure pulse may not reach ambient pressure, or both, thereby resulting in a lower magnitude pressure pulse, which may be desirable in some scenarios. The time units of FIG. 20 may be in second, milliseconds, microseconds, or the like.

In some examples, an extraction cycle uses a predetermined series of pressure pulses with near full vacuum aspiration before the extraction cycle, between individual pulses of relative positive pressure, and after the extraction cycle. The pressure pulses may be selected from a library of pressure pulses having amplitudes and frequencies that facilitate the extraction of clot and other occlusive material. A series of pressure pulses may vary from one another in terms of frequency, amplitude, or both. For instance, a pulsation protocol may use a series of pressure pulses with a trend where one of the amplitude or frequency rises while the other diminishes, where both the amplitude and frequency rise or diminish, or where one of the amplitude or frequency rises or diminishes while the other remains constant.

In some examples, an extraction cycle provides specific pressure pulses based on pressure sensor readings. One such responsive extraction cycle measures pressure within the catheter and then selects one or more pressure pulses optimized for a catheter with those pressure readings. In another responsive extraction cycle, the system cycles through a library of pressure pulse protocols, with time periods of static or full aspiration and occlusion detection after each individual pressure pulse. After the library has been cycled, the system repeats the pressure pulses that were measured to be most successful. The degree of success of a specific pressure pulse is typically commensurate with the amount of increased flow rate after the pressure pulse. The system will continue to cycle down until only a few pressure pulse protocols are in the loop. If the efficacy of the loop begins to diminish, the system will return to the full library and start a fresh cycle.

In an alternative responsive system, a responsive extraction cycle has three modes: Cycling up, where successive pressure pulses are stronger in terms of amplitude and/or frequency, cycling down, where successive pressure pulses are weaker in terms of amplitude and/or frequency, and maintenance pressure pulses, where pressure pulses have a consistent frequency and amplitude. When the system detects a clogged state, it enters the cycling up mode. When the system detects restricted flow state, it enters the maintenance mode. When the system detects an unrestricted flow state, it enters the cycling down mode. In this way, the system trends towards pressure pulses with an amplitude and frequency that facilitates restricted flow, which is beneficially removing clot and other occlusive material.

In situations where maximizing the removal of occlusive material eclipses concerns of blood loss, such as in neurovascular stroke procedures, an alternative embodiment according to the invention may be useful. Under these circumstances, as an example, an optimal technique may include positioning the distal end of a catheter in clot, applying full vacuum, and waiting a predetermined period of time before advancing to a next step. The objective may be complete or nearly complete catheter tip engagement of a mass of occlusive material, engagement which essentially clogs the distal end of the catheter and is sometimes referred to as "corking the catheter". If a clinician has successfully "corked the catheter", the catheter system may be removed from the vessel, withdrawing the mass of clot or occlusion with it. Alternatively, an extraction cycle may be used to draw an occlusion through the catheter lumen or cause the clot to become deeply latched, or corked, within the catheter attached to the present invention. After the completion of the extraction cycle, the clot should be removed or corked in the attached catheter so that the catheter together with the clot can safely be removed from the patient.

In some instances, an extraction cycle may automatically stop or be manually stopped when a clot or other occlusive material clogs a catheter and corks it. For instance, the clot or occlusive substance might be too large or tough to traverse an aspiration catheter, but nonetheless become partially entrained in the aspiration catheter. In such instance, the system may transition to full aspiration to allow the user to remove the corked catheter while dragging the clot or occlusive material out with the catheter. In one example, an extraction cycle is initiated, and the clot or occlusive material still clogs the catheter. The controller may then revert to full aspiration and notify the user of the corking event, whereby the system may prompt the user to remove the catheter. Alternatively, the user may manually turn off an extraction cycle, causing the system to return to full vacuum, and remove the catheter.

To indicate that the present invention is doing work to remove clots or other occlusive material, one embodiment includes visual and/or auditory signals that indicate the progress of a given extraction cycle. In one example, the start of an extraction cycle is signaled by a flashing blue light, which flashes until the cycle is completed, and, at completion, the light turns to green to indicate completion. In another example, base unit 216 may include a light bar.

The light bar fills up incrementally, whereby the light bar progressively "fills up" with light in proportion to the cycle's progress. Alternatively, base unit 216 may include a small screen for displaying images. The small screen may display an animation indicative of loading. Loading animations may execute a repetitive pattern (e.g. spinning circular object) or may execute a single cycle of a prolonged animation (e.g. slowly filling circle). Either in conjunction with visual progress indication or as an alternative to visual progress indication, the system may use auditory cues to signify the extraction cycle's initiation, pulsating phase, and completion. Such auditory cues may include musical notes, beeps, and/or speech. Auditory cues may include updates (e.g. "extracting") or suggestions (e.g. "advance/retract the catheter").

An algorithm may also control a lighting mechanism, e.g. indicator light 210 (FIGS. 7A and 7B), to convey to the user whether the system is in a full aspiration state, an unrestricted flow state, a restricted flow state, a clogged state, a sampling state, or an extracting state. Specific lights may be illuminated to indicate bubbles or that the override switch has been triggered. Additionally, the algorithm may control a piezo acoustic chip that conveys audible information to the physician regarding the state of the effluent and override switch. In one embodiment, the piezo is a surface mounted 4 kHz single tone at 65 dB at 10 cm. The signals may include sounds and phrases such as tone/pitch changes, beeping patterns, "clogged", "occluded", "clot", "blood", "open flow", etc. One example utilizes a dynamic beeping cadence, where a beeping pattern is steadily increased when an unrestricted flow state is increasing in duration. The speed of the beeps indicates the length of time the system has been in unrestricted flow, alerting the physician to the increasingly problematic nature of the system's positioning. The system may also include a multi-position switch or button to specifically activate different algorithms, mute audio cues, or to prime the system with fluid. Such a feature could be activated by inserting a pin in the base unit 210, which will activate this customizable feature.

In one embodiment, the system may be manually powered on and conduct aspiration for a predetermined period of time. If the system detects unrestricted flow, then the on-off valve is turned off to stop flow. The attending physician then must reposition the catheter tip into clot and manually trigger a mechanism (such as a foot pedal or manual switch) to initiate further aspiration. This manual trigger overrides the algorithm and allows aspiration to continue. Once the manual trigger is released, the algorithm again monitors flow to allow aspiration so long as the flow is acceptable. If and when the system again detects unrestricted flow, the on-off valve is again closed until the physician repositions the aspiration catheter and manually overrides the controller. This protocol is repeated until the physician completes the procedure.

Before an aspiration catheter can be used to remove clot and other occlusive material it must be primed with an uncompressible fluid. For instance, a catheter may be filled with saline fluid to remove all the air from the lumen of the catheter. In some embodiments, the present invention automatically primes a catheter, whereby the catheter is filled with fluid to expel all compressible fluids, like air. In one example, the sensors of the present invention monitor catheter contents during use. If compressible fluids are detected, like bubbles, the system may alert the user. In some instances, the system may indicate that the procedure needs to stop so that the catheter can be again primed to remove the air bubbles.

The foregoing examples are not intended to limit the scope of the invention. All modifications, equivalents and alternatives are within the scope of the invention.

The invention claimed is:

1. An aspiration thrombectomy system, comprising:
an aspiration catheter having a proximal end and a distal end, wherein the proximal end of the aspiration catheter comprises a lumen configured to accommodate fluid;
a vacuum source comprising a controllable vacuum valve;
a tubing connected to the aspiration catheter; and
a controller configured to detect a change in a catheter diameter corresponding to a change in the connection between the aspiration catheter and the tubing, wherein the controller is further configured to change a pulsation protocol associated with the aspiration catheter responsive to the change in the catheter diameter, wherein the pulsation protocol specifies pressure variations and pressure patterns to modulate the vacuum valve to change a level of vacuum at the distal end of the aspiration catheter.

2. The aspiration thrombectomy system of claim 1, further comprising:
a pressure source comprising a controllable pressure valve, wherein the pressure source is configured to contain a volume of fluid, and wherein the controller is further configured to modulate the pressure valve according to the pressure variations and pressure patterns specified by the pulsation protocol.

3. The aspiration thrombectomy system of claim 2, wherein the pulsation protocol specifies one or more time periods where both the pressure and vacuum valves are closed.

4. The aspiration thrombectomy system of claim 2, wherein the pulsation protocol specifies a repeated cycle comprising one or more time periods of a pressure-only state in which the vacuum valve is closed and the pressure valve is open.

5. The aspiration thrombectomy system of claim 4, wherein each of the one or more time periods of the pressure-only state is no greater than 50 ms.

6. The aspiration thrombectomy system of claim 2, wherein the tubing acts as a common conduit for fluid communication between the aspiration catheter and the vacuum and pressure sources via the vacuum and pressure valves, respectively.

7. The aspiration thrombectomy system of claim 6, further comprising:
an external unit, wherein the aspiration catheter is connected to the tubing through the external unit.

8. The aspiration thrombectomy system of claim 7, wherein the external unit comprises a switch for operating the aspiration thrombectomy system, and wherein the controller is configured to carry out the pulsation protocol in response to actuation of the switch.

9. The aspiration thrombectomy system of claim 7, wherein the external unit and tubing fluidically connect the proximal end of the aspiration catheter to an output of a valve structure in fluid communication with the pressure source and the vacuum source.

10. The aspiration thrombectomy system of claim 7, wherein the external unit is configured to communicate, with the controller, pulsation protocol data associated with the aspiration catheter.

11. The aspiration thrombectomy system of claim 10, wherein the pulsation protocol data is communicated with the controller responsive to the change in the catheter diameter.

12. The aspiration thrombectomy system of claim 1, wherein the detected change in the catheter diameter corresponds to a change in the connection is between one of a plurality of aspiration catheters and the tubing.

13. The aspiration thrombectomy system of claim 1, wherein the controller is further configured to substantially control flow in and out from the distal end of the catheter.

14. The aspiration thrombectomy system of claim 1, wherein the controller is configured to modulate the vacuum valve according to the pressure variations and pressure patterns specified by the pulsation protocol.

15. The aspiration thrombectomy system of claim 1, wherein the controller is an electronic controller.

16. The aspiration thrombectomy system of claim 1, wherein the controller is separate from the vacuum source.

17. The aspiration thrombectomy system of claim 1, wherein the controller is configured to repeatedly and periodically modulate the vacuum valve to cause the pressure variations and pressure patterns specified by the pulsation protocol.

* * * * *